United States Patent
Masi et al.

(10) Patent No.: US 6,833,465 B2
(45) Date of Patent: Dec. 21, 2004

(54) STABILIZED METALLOCENE COMPOUNDS OF TRANSITION METALS OF GROUP 4 AND PROCESS FOR THEIR PREPARATION

(75) Inventors: Francesco Masi, Sant'Angelo Lodigiano (IT); Anna Sommazzi, Santa Margherita Ligure (IT); Giampietro Borsotti, Novara (IT); Evelina Ballato, Omegna (IT); Roberto Santi, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/670,348

(22) Filed: Sep. 26, 2003

(65) Prior Publication Data

US 2004/0116632 A1 Jun. 17, 2004

(30) Foreign Application Priority Data

Sep. 27, 2002 (IT) ..................................... MI2002A2052

(51) Int. Cl.$^7$ ........................... C07F 17/00; B01J 31/22
(52) U.S. Cl. .......................... 556/53; 526/160; 526/943; 502/152
(58) Field of Search .......................... 556/53; 502/152; 526/160

(56) References Cited

U.S. PATENT DOCUMENTS 6,184,316 B1    2/2001  Masi et al.

FOREIGN PATENT DOCUMENTS

EP      0 801 079    10/1997
WO      WO 95/00526   1/1995

OTHER PUBLICATIONS

Chemical Abstracts, vol. 131, No. 3, p. 596, XP–002238485, JP 11–165075, Jun. 22, 1999.
K. Kasai, et al., Journal of the Chemical Society, Chemical Communications, vol. 1, XP–001148917, pp. 109–110, "Chemoselective Carbon–Carbon Bond Formation Reactions of Zirconacyclopentenes" 1995.
L. Yong, et al., Journal of Molecular Catalysis A: Chemical, vol. 184, No. 1–2, XP–001150381, pp. 147–150, "Organotitanium Chemistry: Substituent Effects on the Dimerization of Isoprene Catalized by Alkenyl–Substituted Cyclopentadientyl Titanium Complexes", 2002.
X. Tao, et al., Journal of Molecular Catalysis A: Chemical, vol. 156, No. 1–2, XP–001150379, pp. 121–126, "Substituent Effect on Oligomerization of Isoprene Catalized by Ring–Substituted (RCp)$_2$TlCl$_2$/i–C$_3$H$_7$MgCl System", 2000.
E.–I. Negishi, et al., Tetrahedron Letters, vol. 25, No. 32, XP–001148892, pp. 3407–3410, "Reaction of Alkenes and Dienes with T–Butylmagnesium Halides and Zirconocene Dihalides. A Convenient Procedure for Hydrozirconation and a Novel T–Butylzirconation of Conjugated Alkenes", 1984.
R. Hara, et al., Tetrahedron Letters, vol. 38, No. 3, XP–004015032, pp. 447–450, "Coupling Reaction of Alkenylzirconocenes with Aryl or Alkenyl Iodides in the Presence of CuCl/Pd(PPh$_3$)$_4$,"Jan. 20, 1997.

*Primary Examiner*—Caixia Lu
(74) *Attorney, Agent, or Firm*—Oblon, Spivak, McClelland, Maier & Neustadt, P.C.

(57) ABSTRACT

A metallocene compound of a metal M of group 4 in the table of elements, comprising a cyclopentadienyl group and at least one oligomeric group R' bonded to M, having the following formula (II):

$$-(A_xD_yU_z)R' \qquad (II)$$

wherein:

A represents any monomeric unit deriving from a vinylaromatic group polymerizable by means of anionic polymerization, having from 6 to 20 carbon atoms;

D represents any monomeric unit deriving from a conjugated diolefin polymerizable by means of anionic polymerization, having from 4 to 20 carbon atoms;

U represents any generic optional monomeric unit deriving from an unsaturated compound copolymerizable with any of the above conjugated diolefins D or vinylaromatic compounds A;

R' represents hydrogen or a hydrocarbyl group having from 1 to 20 carbon atoms, each index "x" and "y" can be independently zero or an integer, provided the sum (x+y) is equal to or higher than 2, preferably between 2 and 50, more preferably between 2 and 25;

"z" can be zero or an integer ranging from 1 to 20.

Said complex can be used for the formation of catalytic systems, in particular for the (co)polymerization of olefins, with enhanced stability and a high activity, so as to enable transportation and storage for prolonged periods of time.

43 Claims, 4 Drawing Sheets

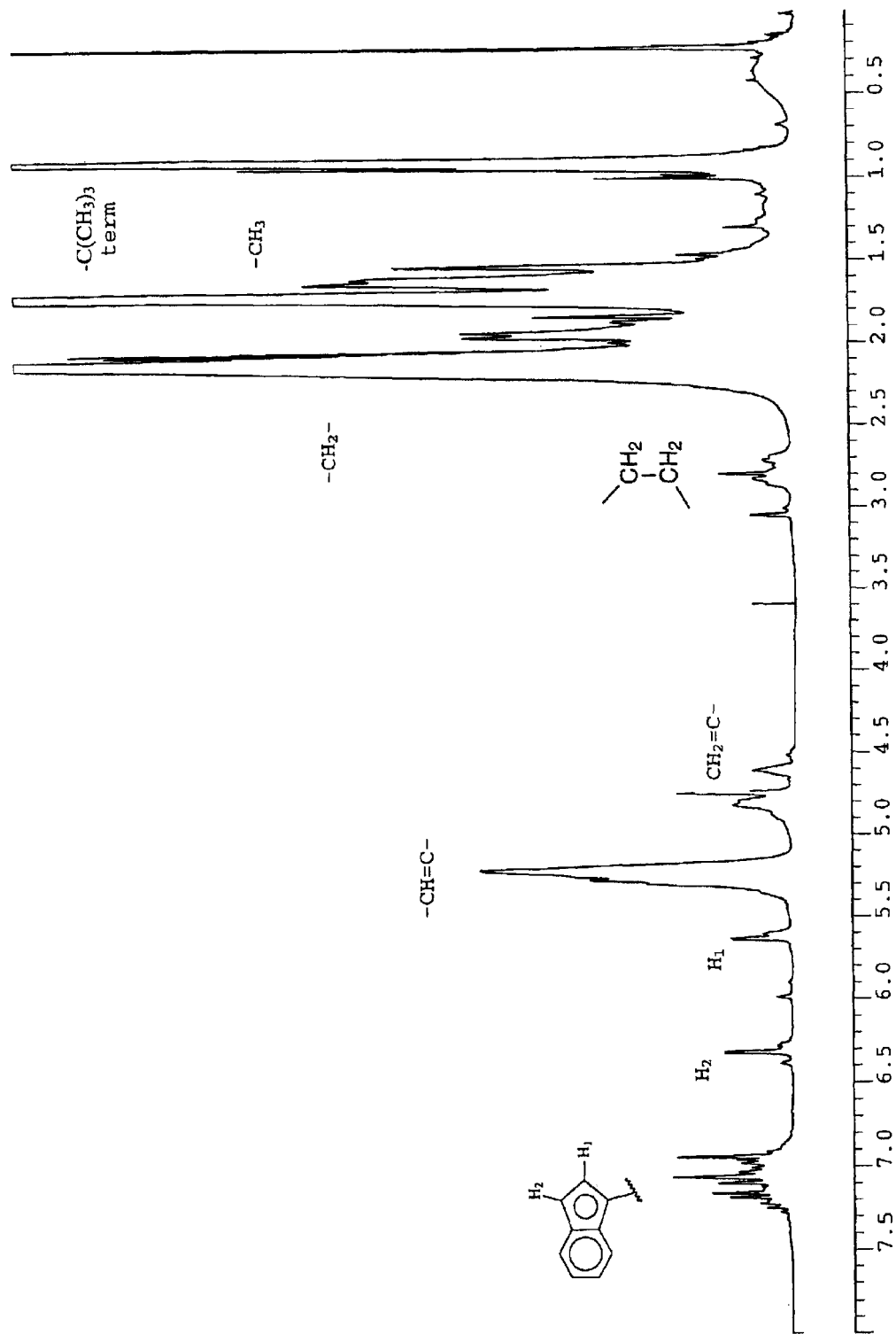
FIGURE 1 : $^1$H NMR spectrum in toluene-D8 of the complex according to example 1

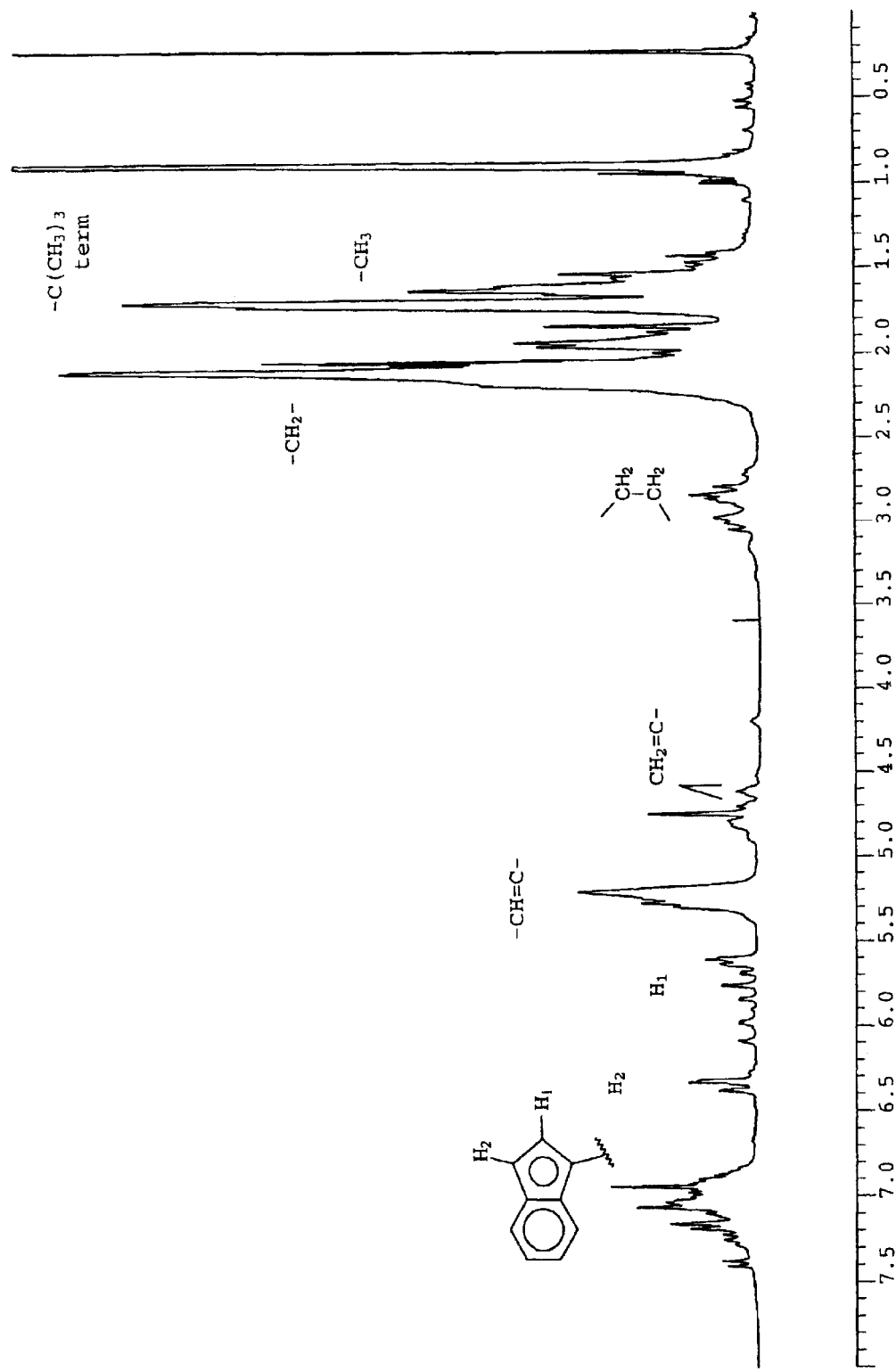
FIGURE 2 : $^1$H NMR spectrum in toluene-D8 of the complex according to example 2

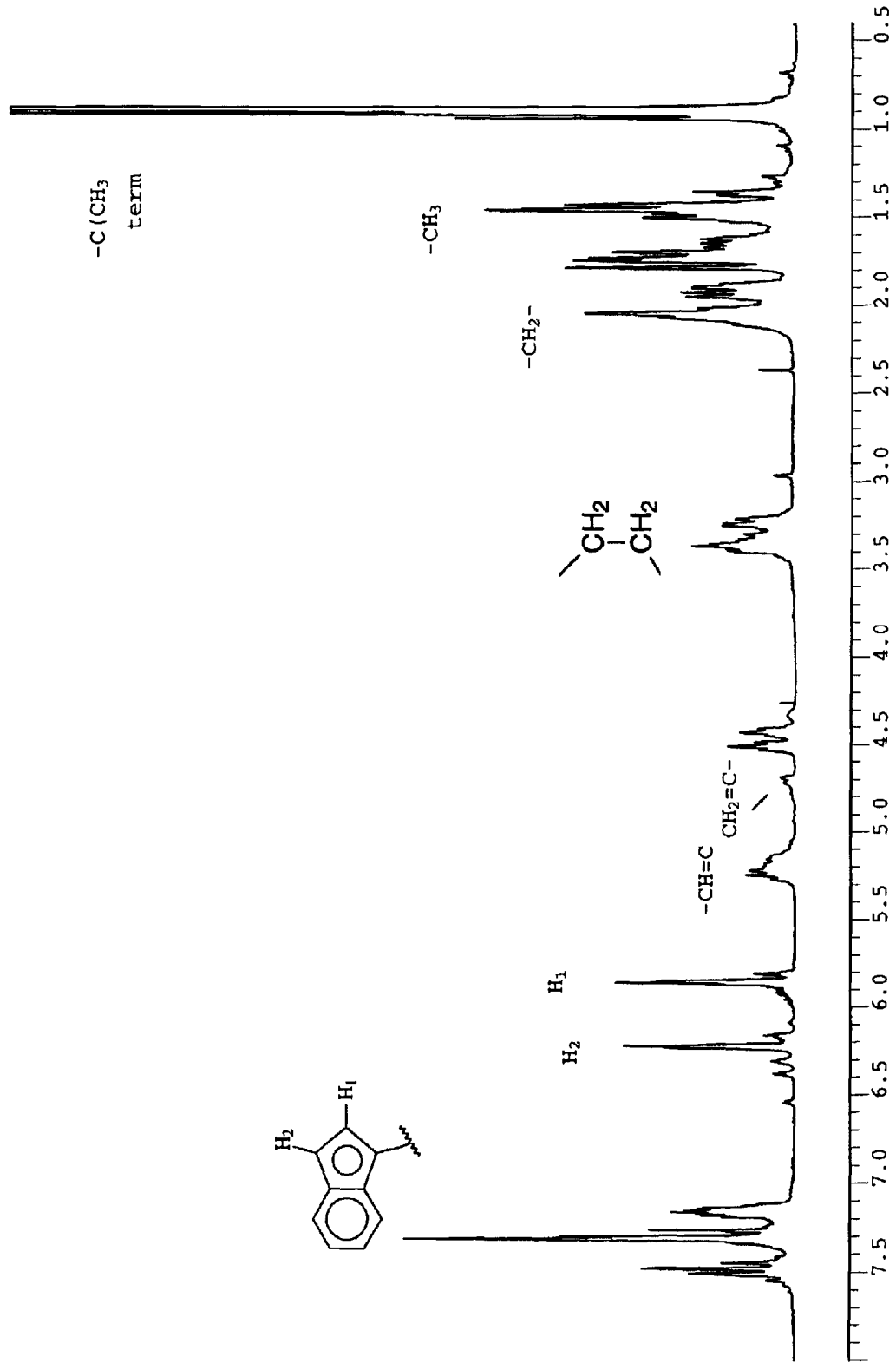
FIGURE 3 : $^1$H NMR spectrum in $CDCl_3$ of the complex according to example 3

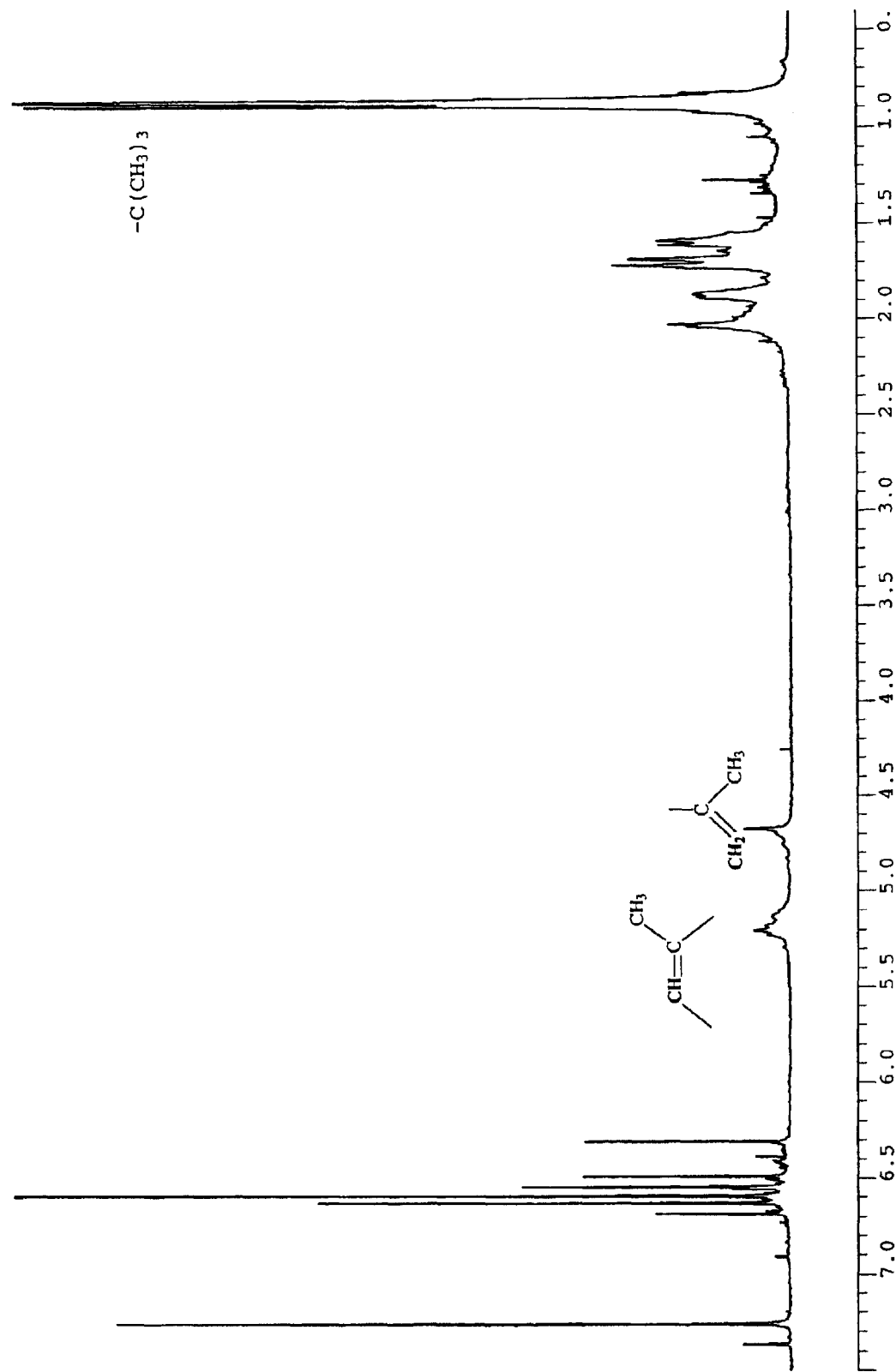
FIGURE 4 : $^1$H NMR spectrum in CDCl$_3$ of the complex according to example 9

STABILIZED METALLOCENE COMPOUNDS OF TRANSITION METALS OF GROUP 4 AND PROCESS FOR THEIR PREPARATION

BACKGROUND OF THE INVENTION

The present invention relates to new stabilized metallocene compounds of transition metals of the fourth group and a process for their preparation.

More specifically, the present invention relates to a group of metallocene complexes which includes stabilized hydrocarbyl groups, used particularly in the formation of catalysts for the (co)polymerization of α-olefins and the hydrogenation of ethylenically unsaturated compounds.

It is generally known in the art that catalysts with a high activity and selectivity in the polymerization of α-olefins can be obtained by combining certain organic oxyderivatives of aluminum (in particular, polymeric methylaluminoxane or MAO) with an $\eta^5$-cyclopentadienyl compound (metallocene) of a transition metal of group four of the periodic table of elements (in the form approved by IUPAC and published in "IUPAC Nomenclature of Inorganic Chemistry, Recommendations 1990", to which reference is also made hereunder). There have been numerous publications on the preparation and use of metallocenes since the eighties; among the first, reference can be made to the description of H. Sinn, W. Kaminsky, in Adv. Organomet. Chem., vol. 18 (1980), page 99 and U.S. Pat. No. 4,542,199.

More recently, catalysts of the metallocene type have been developed in the art, capable of polymerizing olefins also in the absence of organo-oxygenated compounds of aluminum and, in any case, including a lower overall quantity of metals. Said catalytic systems are normally obtained by contact and reaction of a suitable metallocene with an activator consisting of a strong Lewis acid or, more advantageously, of certain organometallic salts whose anion has a delocalized charge and is slightly coordinative, usually a fluorinated tetra aryl borane. Several catalytic systems of this type are described, for example, in the publications of R. R. Jordan in "Advances in Organometallic Chemistry", vol. 32 (1990), pages 325–387, and of X. Yang et al. in "Journal of America Chemical Society", vol. 116 (1994), page 10015, where numerous patent references on the matter, are quoted, together with a wide general survey in the field.

Further catalytic systems, in some way correlated to the preceding ones, are obtained by the reaction of metallocenes and fluoraryl aluminates, as described in international patent application WO 98/0715, which describes the enhancement of the catalytic activity. These catalysts, however, are relatively complex to prepare and are particularly unstable to air and humidity, analogously to those containing boro-anions. Moreover, they cannot be easily obtained from non-alkylated metallocene complexes.

One of the unresolved drawbacks of metallocene catalysts which do not contain aluminoxanes is the relative complexity of the process for their obtainment, as well as various problems relating to their stability. It is well known, in fact, that these catalysts can be obtained by the direct reaction of an alkyl-metallocene, such as, for example, dimethyl bis-indenyl zirconium, with a suitable salt including a boro-anion with a delocalized charge and a cation capable of extracting an alkyl group bonded to the metallocene and forming a neutral and stable molecule. The use of alkyl metallocenes, however, causes serious problems relating to the preservation and stability of these compounds, and consequently the possibility is known of obtaining equally active catalysts also starting from metallocene chlorides but using an alkyl aluminum to form, in situ, an alkyl metallocene. This latter method, however, does not allow full utilization of the metallocene compound, which is partially deactivated, and also requires the use of high quantities of aluminum in the co-catalyst, with a consequent deterioration in the dielectric properties and compatibility with food of the polymeric or hydrogenated products obtained in the presence of said catalysts.

Japanese patent application No. 11-165075 describes certain metallocene complexes of a metal of group 4 comprising two styril or oligostyril groups bonded to the metal. Such complexes are used for the catalytic hydrogenation of olefins.

The production of metallocene catalysts for the polymerization of olefins therefore seems to still have significant drawbacks, in spite of the remarkable progress made with respect to the traditional Ziegler-Natta polymerization, and there seem to be considerable margins for further improvement to meet the increasingly refined demands of industry and the market.

Studies on the structure and synthesis of bis-cyclopentadienyl-allyl complexes of metals of group 4 of the periodic table have been reported in literature, in the publication J. Organomet. Chem., vol. 14, pages 149–156, (1968). In this study, a significant instability of said allyl complexes with time, is observed.

Subsequently, Italian patent application nr. MI00A02776, of the Applicant, describes allyl-metallocene complexes of group 4, showing a significantly improved stability and performance reproducibility. The allyl-metallocene complexes described therein, however, also need particular attention during their synthesis and do not have a completely satisfactory versatility in the formation of the desired catalysts.

SUMMARY OF THE INVENTION

In the continuous attempt to satisfy the above demands with the development of innovative processes and materials, the Applicant has now found a new group of metallocene complexes with stabilizing hydrocarbyl groups in the molecule, which surprisingly allow catalytic systems to be obtained, which are stable enough to allow their transportation and storage for prolonged periods of time and which are also easy to prepare and suitable for the formation of metallocene catalysts, combined both with co-catalysts based on aluminoxanes and with co-catalysts based on ionizing ionic compounds, such as the salts of tetra-aryl boron-anions mentioned above.

A first object of the present invention therefore relates to a metallocene complex of a metal of group 4 of the periodic table, having the following formula (I):

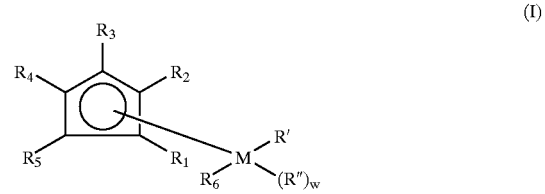

wherein:
M is selected from Titanium, Zirconium and Hafnium, preferably from Titanium and Zirconium, coordinatively bonded to a first $\eta^5$-cyclopentadienyl group;

R' represents an unsaturated, hydrocarbyl group,

R" represents an optional group anionically bonded to the metal M, consisting of an organic or inorganic radical, different from cyclopentadienyl or substituted cyclopentadienyl;

the groups $R_1$, $R_2$, $R_3$, $R_4$, $R_5$, each independently represent, an atom or radical bonded to said first $\eta^5$-cyclopentadienyl group, selected from hydrogen or any other suitable organic or inorganic substituent of said cyclopentadienyl group;

$R_6$ represents any other suitable organic or inorganic group, anionically bonded to the metal M;

"w" has the value of 0 or 1, according to whether the R" group is absent or present in formula (I);

characterized in that said R' group consists of an unsaturated oligomeric group having the following formula (II):

$$-(A_xD_yU_z)R^I \qquad (II)$$

wherein:

A represents any monomeric unit deriving from a vinylaromatic group polymerizable by means of anionic polymerization, having from 6 to 20 carbon atoms;

D represents any monomeric unit deriving from a conjugated diolefin polymerizable by means of anionic polymerization, having from 4 to 20 carbon atoms;

U represents any generic optional monomeric unit deriving from an unsaturated compound co-polymerizable with any of the above conjugated diolefins D or vinylaromatic compounds A;

$R^I$ represents hydrogen or a hydrocarbyl group having from 1 to 20 carbon atoms, each index "x" and "y" can be independently zero or an integer, provided the sum (x+y) is equal to or higher than 2, preferably between 2 and 50, even more preferably between 2 and 25;

"z" can be zero or an integer ranging from 1 to 20;

with the proviso that, when $R_6$ is a $\eta^5$-cyclopentadienyl or substituted $\eta^5$-cyclopentadienyl group and R' is $-(A_x)R^I$, R" is different from $-(A_x)R^I$.

A simple, high-yield process for the preparation of said complexes having formula (I), constitutes a second object of the invention.

Any further possible objects of the present inventions will appear evident from the following description and examples.

DETAILED DESCRIPTION

The term "(co)polymerization of α-olefins" as used in the text and claims, refers to both the homo- and co-polymerization of α-olefins between each other or with a different ethylenically unsaturated compound, polymerizable with α-olefins.

The term "suitable", as used in the text and claims, with reference to groups, radicals and substituents in the formulae of organic and organometallic compounds, means that said groups, radicals and substituents are compatible with the stability characteristics of said compounds in the pure state, i.e. substantially inert with respect to the whole molecule under examination or any part thereof, on the basis of the characteristics of chemical reactivity generally known to average technical experts in the field.

The term "derivative", as used herein with reference to monomeric units, means the attainment of said units in accordance with one of the known anionic poly-addition reactions, with both a 1–2 and, when possible, 1–4 mechanism. The monomeric units thus obtained essentially have the same structure as the monomer from which they derive, but with one unsaturation less, and are bonded by a covalent bond to both ends of the oligomeric chain to which they belong.

The complex having formula (I), in accordance with the present invention, is a metallocene complex of a metal of the $4^{th}$ group of the periodic table, and is characterized by an enhanced stability in solution or in the pure state, as well as by a specific reactivity during the formation of catalytic compositions suitable for promoting (co)polymerization processes of α-olefins and the hydrogenation of olefinically unsaturated compounds. Without limiting in any way the present invention to any particular theory or interpretation, we feel that the advantageous and surprising characteristics of said complexes having formula (I) with respect to the mono- or bi-metallocene complexes of the known art, can be specifically attributed to the presence of at least one unsaturated group having formula (II), bonded to the metal M.

In accordance with the previous definition of the complex having formula (I), the metal M can be selected from titanium, zirconium and hafnium, preferably from titanium and zirconium. In particular, according to a certain aspect of the present invention, the compounds having formula (I), wherein the metal M is titanium in the oxidation state +3 and "w" is zero, i.e. the optional group R" is absent, have proved to be more advantageous for the formation of hydrogenation catalysts. Certain compounds having formula (I), on the contrary, wherein M is Ti or Zr, more preferably Zr, in oxidation state +4, and "w" is 1, have proved advantageous for the formation of some catalytic compositions for the (co)polymerization of α-olefins, without in any way excluding the use in said processes of catalysts obtained from compounds with M in oxidation state +3. It has also been found that mixtures of two or more complexes having formula (I) can be advantageous for particular uses in the field of (co)polymerization, possibly comprising two or even three different metals M, with the same or different oxidation state, such as, for example, Ti(III) and Hf(IV) or Zr(IV) and Hf(IV), which are however included in the scope of the present invention.

In accordance with the widest sense of the present invention, the group R', schematically represented with the above formula (II), is an unsaturated group consisting of several monomeric units of the A and/or D, and possibly U type, as specified above, without any limitation of formula or chain sequence. In this sense, said formula (II) must be interpreted in the most general meaning of empirical formula of said oligomeric group, with no limitation in the sequence of said monomeric units or group of monomeric units. Moreover, as said oligomeric groups having formula (II) can be obtained through anionic polymerization under controlled conditions, said formula (II) must be necessarily interpreted, according to common practice, as being representative of a mixture of compounds deriving from a polymerization process and consequently having a varying number of units, distributed around an average value which represents the average polymerization degree. The unsaturations can be of the olefin type, in the D monomeric units deriving from a diene, or of the aromatic type, in the A units deriving from a vinylaromatic compound.

Oligomeric groups having formula (II), in accordance with the present invention, can consist of a single block of two or more D units in a sequence, resulting from a single conjugated diolefin, possibly partially polymerized with a 1–4 mechanism and partially with a 1–2 mechanism, according to what is known from the anionic polymerization technique, or from a single block of two or more A units in a sequence, resulting from a single vinylaromatic compound.

Oligomeric groups consisting of at least two monomeric units A or at least two monomeric units D, different from each other, deriving from two or more conjugated diolefins or two or more vinylaromatic compounds, are also included in formula (II).

Oligomeric groups consisting of at least one monomeric unit D resulting from a conjugated diolefin, at least one monomeric unit A resulting from a vinylaromatic compound and possibly at least one co-polymerizable unit U, are also included in formula (II). Said oligomeric groups can have a statistical distribution of the different monomeric units, or can consist of more or less homogeneous blocks of units A or D or U, bonded to one another.

According to a particular aspect of the present invention, said formula (II) represents a block oligomer, preferably di-block, wherein a first block can be distinguished, made up of D units alone, bonded to each other, said first block, in turn, being bonded to a second block essentially made up of A units alone. Through particular methods, known in the anionic co-polymerization technique for obtaining elastomers, it is also possible to obtain three-block structures, one of A units alone, one of D units alone and the third consisting of A and D units in statistical sequence (called "tapered" according to the known art). The sequence with which the blocks are bonded to each other and to the metal M and to the group $R^I$, respectively, at the chain ends, can be easily selected by an average expert, on the basis of the polymerization techniques available, as can be seen hereunder. The block D is preferably bonded to the metal M.

Typical diolefins polymerizable via anionic polymerization to form monomeric units of the D type, are 1,3-diolefins with 4 to 20, preferably 4 to 10 carbon atoms, such as, for example, 1,3-butadiene, isoprene, chloroprene, 2,3-dimethyl-1,3-butadiene, 1,3-pentadiene, 2-methyl-1,3-pentadiene, 1,3-hexadiene, 4,5-diethyl-1,3-octadiene, 3-butyl-1,3-octadiene, or certain cyclodiolefins, such as, for example, 1,3-cyclohexadiene.

Typical vinyl aromatic compounds polymerizable through anionic polymerization to form monomeric units of the A type, are compounds wherein a group of an aromatic nature (also hetero-aromatic) is bonded in α position to a vinyl group, i.e. a primary olefin group, for example styrene, 4-tert-butyl styrene, α-methyl styrene, o-methyl styrene, p-methyl styrene, vinyl naphthalene, 2-vinyl furan and 2-vinyl pyridine. Preferred vinyl aromatic compounds are hydrocarbyl compounds having from 8 to 15 carbon atoms, preferably styrene.

Acrylic and methacrylic esters, such as methyl methacrylate, ethyl methacrylate, acrylonitrile, methyl acrylate, t-butyl acrylate, methyl-2-ethyl acrylate, methyl-2-phenyl acrylate are, for example, typical compounds polymerizable with the previous ones to form monomeric units of the U type.

Particularly preferred R' groups are those wherein the sum of the indexes (x+y+z) is between 2 and 15. According to a particular aspect, "z" is equal to 0 and (x+y) is between 2 and 15. According to another particular aspect, "x" and "z" are both equal to 0 and said R' group consists of an oligomer of a conjugated diene D with an average polymerization degree ranging from 2 to 15.

The $R^I$ group in formula (II) preferably represents an aliphatic, cycloaliphatic, aromatic or alkyl aromatic group having from 1 to 20, preferably from 2 to 10, more preferably from 3 to 6, carbon atoms and derives from the organic residue of the polymerization initiator in the preparation process of said oligomeric group having formula (II). Typical, non limiting examples of the group $R^I$ are tert-butyl, n-butyl, isopropyl, n-hexyl, cyclohexyl, benzyl, phenyl, toluyl.

The R" group in formula (I) can have any of the general or specific meanings normally attributed to it in technical literature of the field, with reference to a non-cyclopentadienyl substituent of the metal M in a metallocene complex. It can therefore be inorganic or organic, of a more or less anionic nature, according to the relative electro negativity of its atoms. A second end of this group can also be bonded to the group $R_6$ in formula (I), to form an overall cyclic structure including the metal M, as, for example, in the case of a divalent tetramethylene —$(CH_2)_4$—, group or the group 1,4-tetramethylene-dioxide —O—$(CH_2)_4$—O—.

Non-limiting examples of groups of substituents which can be represented, in this case, by R" are: hydrogen, halogen such as chlorine or bromine, an alkyl or alkyl aryl $C_1$–$C_{2o}$ group, an allyl $C_3$–$C_{2o}$ group, an alkyl silyl $C_3$–$C_{2o}$ group, a cycloalkyl $C_5$–$C_{2o}$ group, an aryl or aryl alkyl $C_6$–$C_{2o}$ group, an alkoxide or thioalkoxide $C_1$–$C_{2o}$ group, a carboxylate or carbamate $C_2$–$C_{2o}$ group, a dialkyl amide $C_2$–$C_{2o}$ group and an alkyl silylamide $C_4$–$C_{2o}$ group. Typical examples are hydride, halide, especially chloride or bromide, a linear or branched alkyl group such as methyl, ethyl, isopropyl, isoamyl, octyl, decyl, benzyl, an alkyl silyl group such as, for example, trimethyl silyl, triethyl silyl or tributyl silyl, a cycloalkyl group such as cyclopentyl, cyclohexyl, 4-methyl cyclohexyl, an aryl group such as phenyl or toluyl, an alkoxyl or thioalkoxyl group such as methoxyl, ethoxyl, iso- or sec-butoxyl, ethyl sulfide, a carboxylate group such as acetate, trifluoro acetate, propionate, butyrate, pivalate, stearate, benzoate or, again, a dialkyl amide group such as diethyl amide, dibutyl amide, or alkylsilyl amide such as bis(trimethyl silyl)amide or ethyl trimethyl silylamide. Among the above, hydrogen and organic alkyl, alkyl amide and alkyl silyl groups having from 1 to 20 carbon atoms, are preferred.

According to a particularly preferred aspect of the present invention, both groups R' and R" are, independently, oligomeric groups having formula (II). Metallocene complexes of this type show a particularly high stability, but also maintain excellent activities when used as catalyst components. The two groups R' and R" can represent two different groups having formula (II) bonded to the same metal M, or, even more preferably, they can substantially have the same formula as they have been obtained through the same anionic polymerization process, with the proviso that, when $R_6$ is a $\eta^5$-cyclopenta-dienyl or substituted $\eta^5$-cyclopentadienyl group and R' is -$(A_x)R^I$, R" is different from -$(A_x)R^I$. When necessary, said complexes can also include the two groups R' and R" having the same terminal group $R^I$ in common, so as to form a cyclic structure with the metal M. Complexes of this type can be obtained starting from a living dianionic group, as specified in more detail hereunder.

Each or said atoms or radicals $R_1$, $R_2$, $R_3$, $R_4$, $R_5$, bonded to a first $\eta^5$-cyclopentadienyl group in the complex having formula (I), can independently be hydrogen, halogen or any hydrocarbyl group having from 1 to 20, preferably from 1 to 10, carbon atoms, substituted, when necessary, with suitable hetero-atoms such as, for example, Si, Ge, O, F, Cl or Br. Typical, non limiting, examples of these radicals are: hydrogen, methyl, ethyl, propyl, isopropyl, butyl, sec-butyl, isobutyl, tert-butyl, hexyl, 2-ethyl butyl, octyl, decyl, dodecyl, hexadecyl, octadecyl, cyclohexyl, methyl cyclohexyl, ethyl cyclohexyl, 2,4,6-trimethyl cyclohexyl, octyl cyclohexyl, phenyl, methyl-phenyl, ethyl-phenyl, biphenyl, 2,4,6-trimethyl phenyl, octyl-phenyl, benzyl, 4-methyl benzyl, biphenyl methyl, trifluoro-methyl, perfluoro-ethyl, pentafluoro-phenyl, 3,4,5-trifluoro-phenyl, dichloro-phenyl, chlorofluoro-phenyl, trichloro-methyl, 2-methoxy-ethyl, 2-trifluoro-methoxyethyl, 4-methoxy-phenyl and 4-ethoxy-phenyl, trimethyl silyl, triethyl silyl.

Moreover, analogously to what is already known in technical literature in relation to other cyclopentadienyl complexes of the metals of group 4 of the periodic table, two or even more of said radicals having suitable structures, can be bonded to each other to give a cyclic, or even poly-cyclic, saturated, unsaturated or aromatic structure, having at least one common bond "condensed"(according to the term normally used) with said cyclopentadienyl ring. In accordance with the present invention, indenyl and fluorenyl groups, possibly further substituted, and the corresponding groups obtained by hydrogenation of their aromatic rings, are non-limiting examples of said condensed cyclic structures.

Moreover, according to the present invention, any radical or condensed group bonded to said first $\eta^5$-cyclopentadienyl group can, in turn, be covalently bonded to said group $R_6$ to form a cyclic, so-called "bridged" structure, according to the wording currently used in the field, which also includes said metal M in the cycle.

Typical, non-limiting examples of said first cyclopentadienyl group in formula (I) are: cyclopentadienyl, 1,2,3-trimethyl cyclopentadienyl, 1,2,4-trimethyl cyclopentadienyl, pentamethyl cyclopentadienyl, indenyl, fluorenyl, 4,5,6,7-tetrahydroindenyl, 1,3-dimethyl-4,5,6,7-tetrahydroindenyl, 1,2,3-trimethyl indenyl, octahydrofluorenyl, the benzocycloalkyl pentadienyl groups described in Italian patent application Nr. MI00A000680.

Said $R_6$ group having formula (I), according to the present invention, represents, in its most general form, any organic or inorganic group bonded to the metal M, of a more or less anionic nature, according to the relative electro-negativity of its atoms, analogously with the usual definition of a generic ligand of the metal in a metallocene complex. $R_6$ can have, for example, any of the previously mentioned meanings for the R" group. It can be hydrogen, a halogen or an alkyl, cycloalkyl, aryl, alkoxy, aryloxy, amide or carboxy group, having from 1 to 30, preferably from 1 to 20, carbon atoms. A second chain-end of $R_6$ can also be joined to the group R", or preferably to said first cyclopentadienyl group in formula (I), to form an overall cyclic structure including the metal M, as, for example, in the case of a divalent tetramethylene —$(CH_2)_4$— group, or the group 1,4-tetramethylenedioxide —O—$(CH_2)_4$—O—, 1,2-ethylenebis-$\eta^5$-cyclopentadienyl groups.

Non-limiting examples of substituent groups which can be represented, in this case, by $R_6$ are, hydride, halide such as chloride or bromide, an alkyl or alkylaryl $C_1$–$C_{20}$ group, an allyl $C_3$–$C_{20}$ group, an alkylsilyl $C_3$–$C_{20}$ group, a cycloalkyl $C_5$–$C_{20}$ group, an aryl or arylalkyl $C_6$–$C_{20}$ group, an alkoxide or thioalkoxide $C_1$–$C_{20}$ group, a carboxylate or carbamate $C_2$–$C_{20}$ group, a dialkylamide $C_2$–$C_{20}$ group and an alkylsilylamide $C_4$–$C_{20}$ group. Typical examples are: hydride, methyl chloride, ethyl, butyl, isopropyl, isoamyl, octyl, decyl, benzyl, trimethyl silyl, triethyl silyl or tributyl silyl, cyclopentyl, cyclohexyl, 4-methylcyclohexyl, phenyl or toluyl, methoxyl, ethoxyl, iso- or sec-butoxyl, ethyl sulfide, acetate, trifluoro acetate, propionate, butyrate, pivalate, stearate, benzoate, diethyl amide, dibutyl amide, bis(trimethyl silyl) amide or ethyl trimethyl silylamide. Among the above-mentioned products, hydrogen and the organic alkyl, alkyl amide and alkyl silyl groups having from 1 to 20 carbon atoms, are preferred.

According to a particular, preferred aspect of the present invention, said $R_6$ includes a second cyclopentadienyl group, $\eta^5$-coordinated to metal M, and can also be optionally bonded, by means of a covalent bond, to any non-monovalent atom of said first cyclopentadienyl group, preferably in substitution of the group $R_1$, to form, as mentioned above, a bridged cyclic structure including the same metal M. In particular, said $R_6$ group can have the following formula (III):

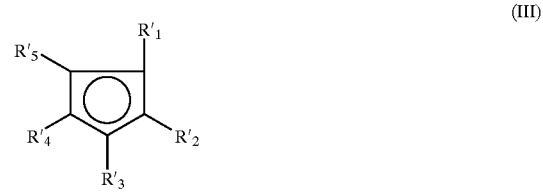

(III)

wherein each of the different $R'_1$, $R'_2$, $R'_3$, $R'_4$, $R'_5$, groups is independently selected from any of the different meanings previously mentioned with reference to the $R_1$, $R_2$, $R_3$, $R_4$, $R_5$ groups of said first cyclopentadienyl group. When said group having formula (III) is bonded to said first cyclopentadienyl group to form a so-called "bridged" cyclic structure, said $R_1$ and $R'_1$ groups preferably form together a divalent group having 1 to 20, preferably 2 to 15 carbon atoms and possibly also containing atoms selected from silicon germanium and halogens, particularly fluorine. Typical, non-limiting examples of said divalent groups are methylene, 1,2-ethylene, 1,3-propylene, 1,4-butylene, 1,4-but-2-enylene, dimethyl silylene, diethyl silylene, 1,2-tetramethyldisilylene, 1,2-xilylene, 1,3-xilylene, 1,2-phenylenemethylene, dimethyl germylene, 1,3-cyclohexylene.

Non-limiting examples of the groups $R'_1$, $R'_2$, $R'_3$, $R'_4$, $R'_5$, are hydrogen, methyl, ethyl, propyl, isopropyl, butyl, sec-butyl, isobutyl, tert-butyl, hexyl, 2-ethyl butyl, octyl, decyl, dodecyl, hexadecyl, octadecyl, cyclohexyl, methyl cyclohexyl, ethyl cyclohexyl, 2,4,6-trimethyl cyclohexyl, octyl cyclohexyl, phenyl, methyl-phenyl, ethyl-phenyl, biphenyl, 2,4,6-trimethyl phenyl, octyl-phenyl, benzyl, 4-methyl benzyl, biphenyl methyl, trifluoro-methyl, perfluoro-ethyl, pentafluoro-phenyl, 3,4,5-trifluoro-phenyl, dichloro-phenyl, chlorofluoro-phenyl, trichloro-methyl, 2-methoxy-ethyl, 2-trifluoro-methoxyethyl, 4-methoxy-phenyl and 4-ethoxy-phenyl, trimethyl silyl, triethyl silyl.

According to another aspect of the present invention, $R_6$ represents an organic group bonded to the metal M by means of an atom selected from N, P, O or S, for example, any amido group having the formula $R_7R_8N$—, phosphido group having the formula $R_7R_8P$—, oxy group having the formula $R_7O$—, thio of formula $R_7S$—, wherein said $R_7$ and $R_8$ groups can have any of the meanings specified above for any of the groups $R'_1$, $R'_2$, $R'_3$, $R'_4$, $R'_5$. Among these, those groups wherein $R_7$ is a divalent group, preferably having from 1 to 5 carbon atoms, bridged also to said cyclopentadienyl group in formula (I), in substitution of $R_1$, have proved to be of particular interest.

Complexes having formula (I) wherein said first and second cyclopentadienyl group are the same, are particularly preferred, according to the present invention, due to the simplicity of their preparation. Among these, bis (tetrahydroindenyl) complexes, optionally alkyl-substituted on the cyclopentadienyl ring, or bonded to each other by means of a divalent "bridged" group, according to the above description, have been found to be even more advantageous, for the purposes of the present invention.

According to a further particular aspect of the present invention, said $R_6$ group can represent another oligomeric group having formula (II), to form a metallocene complex which comprises said first cyclopentadienyl group and two or three oligomeric groups having formula (II), respectively, depending on whether the metal M has oxidation state (III) or (IV).

Non-limiting examples of complexes having formula (I), in accordance with the present invention, are listed below:

$Cp_2Zr[((D_{C5H8})_3A_{C8H8})_3Pr^i]_2$  $Cp_2Zr[((D_{C5H8})_3A_{C8H8})_3Pr^i]_2$
$Cp_2ZrCl[(A_{C8H8})_3Bu^t]$  $Cp_2ZrCl[((D_{C5H8})_3A_{C8H8})_5Pr^i]$
$Cp_2ZrCl[(A_{C8H8})_{10}Pr^i]$  $Cp_2ZrCl[((D_{C5H8})_3A_{C8H8})_{10}Pr^i]$
$Cp_2Zr[(D_{C5H8})_{20}Bu^t]_2$  [o-Xen-$(Cp)_2]Zr[(D_{C5H8})_4Bu^t]_2$
[o-Xen-$(Cp)_2]Zr[(D_{C4H6})_4Bu^t]_2$  $Cp_2ZrCl[(B_{C4H6})_3Pr^i]$
$[Ph_2Si(\eta^5-Ind)_2]Zr[(D_{C5H8})_3Pr^i]_2$  $[1,2-en(\eta^5-Ind)_2]ZrCl[(A_{C8H8})_3Bu^t]$
[o-Xen-$(\eta^5-(THInd)_2]Ti[(D_{C5H8})_{15}Bu^t]$  $(\eta^5-Ind)Ti[(D_{C5H8})_5Bu^t]$
[o-Xen-$(\eta^5-(THInd)_2]ZrCl[(D_{C5H8})_9Bu^t]$  $Cp_2Zr[(D_{C5H8})_3Pr^i]_2$
o-Bzn-[1-($-\eta^5$-THInd)$_2]Zr[(D_{C5H8})_5Bu^t]_2$  o-Bnz-$[\eta^5-C_5Me_4]Zr[(D_{C5H8})_5Bu^t]_2$
$[1,2-en(\eta^5-Ind)_2]Zr[(D_{C5H8})_3Pr^i]_2$  $[1,2-en(\eta^5-Ind)_2]ZrCl[(D_{C5H8})_3Bu^t]$
$\eta^5-(THInd)_2ZrCl[(D_{C5H8})_5Pr^i]$  $\eta^5-(Ind)_2Zr[(D_{C5H8})_7Bu^n]_2$
$[Me_2Si(\eta^5-C_5Me_4)(NBu^t)]Ti[(D_{C5H8})_{10}Pr^i]$  $(Cp)_2Ti[(D_{C5H8})_5Pr^i]$
$[Me_2Si(\eta^5-C_5Me_4)(NBu^t)]Ti[(D_{C5H8})_{10}Pr^i]_2$  $(Cp)_2Ti[(B_{C4H6})_7Pr^i]$
$[1,2-en(\eta^5-Ind)_2]Ti[(D_{C5H8})_5Pr^i]$  $(\eta^5-C_5Me_5)_3Ti[(B_{C4H6})_{10}Pr^i]$
$[\eta^5-(2,4-CF_3)_2Bz)C_5H_4]_2ZrCl[(D_{C5H8})_3Bu^t]$  $[Pro^i(Cp)(\eta^5-Flu)]Ti[(D_{C5H8})_5Bu^t]_2$
o-Bzn-$[\eta^5-1-(3-Me)Ind]_2Hf[(D_{C5H8})_5Bu^t]_2$  $[Me_2Si(\eta^5-C_5H_4)_2]Hf[(D_{C5H8})_5Bu^t]_2$
$[Pro^i(Cp)(\eta^5-Flu)]Zr[(D_{C5H8})_{15}Bu^t]_2$  $(\eta^5-Ind)Zr[(D_{C5H8})_3Pr^i]_3$
o-Bzn-$[\eta^5-1-(4,7-Me_2)Ind]_2Ti[(D_{C5H8})_5Pr^i]$  $(\eta^5-Ind)ZrCl[(D_{C5H8})_3Pr^i]_2$
$[Pro^i(Cp)(\eta^5-Flu)]Zr[(D_{C5H8})_{10}Pr^i]_2$  $(\eta^5-C_5Me_5)Zr[(A_{C8H8})_{10}Pr^i]_3$
$[1,2-en(\eta^5-THInd)_2]Zr[((D_{C5H8})_3A_{C8H8})_3Pr^i]_2$  $Cp_2Zr[((D_{C5H8})_3A_{C8H8})_{10}Pr^i]_2$
$[\eta^5-(4-F-Ph)C_5H_4]_2Zr[(B_{C4H6})_5Bu^t]_2$  $Cp_2ZrCl[(D_{C5H8})_{10}Pr^i]$
$[\eta^5-(2,4-CF_3)_2Bz)C_5H_4]_2ZrCl[(D_{C5H8})_3Bu^t]_2$  $(\eta^5-Ind)Ti[(B_{C4H6})_7Pr^i]_3$
$[Me_2Si(CH_2-\eta^5-C_5H_4)_2]Zr[(D_{C5H8})_8Bu^t]_2$  $(\eta^5-C_5Me_5)Ti[(D_{C5H8})_5Bu^t]_3$
[o-Xen-$(Cp)(\eta^5-Flu)]Zr[(D_{C5H8})_5Bu^t]_2$  $Cp_2ZrCl[(A_{C8H8})_3Pr^i]$
$[Me_2Si(CH_2)_2-\eta^5-Ph-C_5H_3)_2]Zr[(B_{C4H6})_5Bu^t]_2$  $Cp_2ZrCl[(B_{C4H6})_3Pr^i]$
o-Bzn-$[\eta^5-1-(5,6-Me_2)Ind]_2Zr[(B_{C4H6})_{10}Bu^t]_2$  $Cp_2Zr[(B_{C4H6})_5Pr^i]_2$
o-Bzn-$[\eta^5-1-(4,7-Me_2)Ind]_2Zr[(B_{C5H6})_5Bu^t]_2$  $Cp_2Zr[(B_{C4H6})_3Bu^t]_2$
$[Me_2Si(\eta^5-1-Ind)_2]Hf[((D_{C5H8})_3A_{C8H8})_3Pr^i]_2$  $CpTi[(D_{C5H8})_3(A_{C8H8})_3Pr^i_2$
$[Me_2Si(\eta^5-THInd)_2]Hf[((D_{C5H8})_3A_{C8H8})_3Ph]_2$  $(Cp)_2Zr[(D_{C5H8})_3Bu^n]_2$
o-Bzn-$[\eta^5-1-(3-Me)Ind]_2HfCl[(D_{C5H8})_5Bu^t]$  $Cp_2ZrCl[(D_{C5H8})_3Pr^i]$
$[\eta^5-(3,5-(CF_3)_2Bz)C_5H_4]_2Ti[(B_{C4H6})_7Pr^i]$  $[1,2-en(\eta^5-Ind)_2Ti](D_{C5H8})_5Bu^t]$
$[\eta^5-1,3-(CF_3)_2C_5H_3]Ti[(D_{C5H8})_5Bu^t]_2$  $(\eta^5-THInd)_2Zr[(D_{C5H8})_5Pr^i]_2$
$[\eta^5-(4-CF_3Bz)C_5H_4]_2Ti[(D_{C5H8})_3Bu^n]_2$  $(\eta^5-Ind)_2Zr[(D_{C5H8})_6Bu^{it}]_2$
$[Pro^i(Cp)(\eta^5-Flu)]Zr[(D_{C5H8})_3(A_{C8H8})_3Pr^i]_2$  $Cp_2Zr[(D_{C5H8})_{10}Pr^i]_2$
o-Bzn-$[\eta^5-1-(4,7-diphenyl)Ind]_2Zr[(B_{C4H6})_5Bu^t]_2$
$[1,2-en(\eta^5-1-(2,4-(CF_3)_2Bz)Ind)_2]Zr[(D_{C5H8})_5Bu^t]_2$ Caption: Cp=$\eta^5$-cyclopentadienyl; $Pr^i$=isopropyl; $D_{C5H8}$=monomeric unit deriving from isoprene; $A_{C8H8}$=monomeric unit deriving from styrene; $B_{C4H6}$=monomeric unit deriving from butadiene; $Bu^n$=normal butyl; $Bu^t$=tert-butyl; Me=methyl; Et=ethyl; Bz=benzyl; $Pro^i$=2,2-isopropylidene; Ph=phenyl; Ind=indenyl; THInd=4,5,6,7-tetrahydro indenyl; Flu=fluorenyl; 1,2-en=1,2-ethylidene; $Ph_2Si$=biphenyl silylene; $Me_2Si$=dimethyl silylene; o-Xen=ortho-xylylene, o-Bzn=ortho-benzylidene.

Any mixture or composition comprising at least one of said complexes having formula (I), in particular any mixture of two or more of said complexes having formula (I), is also included in the scope of the present invention.

Metallocene polynuclear compounds consisting of two or more metallocene compounds, each of which has a structure corresponding to a compound included in the above formula (I), joined to each other through one or more covalent bonds between two or more groups bonded to each metal, are not excluded from the scope of this invention, as they are obvious equivalents of the same.

Complexes having formula (I) comprising one or more neutral coordinating compounds, normally called Lewis bases, intentionally not represented in formula (I), solely for the sake of descriptive simplification, are also not excluded from the scope of the present invention. Said Lewis bases, as is well known, can form stable adducts, which can be isolated in pure form, or a coordination sphere in solution, with complexes showing a coordinative deficiency, such as those in accordance with the present invention.

According to another aspect of the present invention, the above-mentioned complexes having formula (I) can also be supported on suitable solids, such as, for example, certain active materials such as magnesium chloride, in polymerizations of the Ziegler-Natta type, or inert materials, preferably including Si and/or Al oxides such as, for example, silica, alumina or silico-aluminates, in order to produce solid components for catalysts, more convenient than the corresponding soluble catalysts in certain industrial processes, as they allow, for example, the catalyst to be easily separated, by filtration, from the reaction product. For supporting said complexes, technical experts in the field can refer to any of the known techniques, normally including contact, in a suitable inert liquid medium, between said complex having formula (I) and the carrier, possibly activated by heating to temperatures higher than 200° C. or by contact with other components, such as organometallic compounds such as aluminum alkyls, coordinating compounds such as alcohols, amines, phosphines and other Lewis bases. Complexes and catalytic systems based thereon, which have been supported on a solid component by the functionalization of the latter and formation of a covalent bond between the solid component and a metallocene complex included in the previous formula (I), are also included in the scope of the present invention.

The complexes according to the present invention can be prepared according to the methods and processes typical of organometallic chemistry. In particular, they can be prepared by means of a process which includes the reaction of a suitable oligomeric organometallic compound with a suitable metallocene precursor, according to the procedure of a nucleophilic substitution reaction, as described, for example, in the publication "Comprehensive Organometallic Chemistry", Pergamon Press Ltd., vol. 3, pages 331–426, 560–599 (1982).

A second object of the present invention therefore relates to a process for the preparation of a metallocene complex having the above formula (I), which comprises the contact and reaction, in suitable proportions, of a metallocene precursor having the following formula (IV):

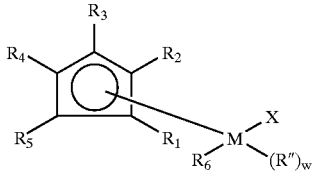

(IV)

wherein: the different symbols M, R", $R_1$, $R_2$, $R_3$, $R_4$, $R_5$, $R_6$, and "w" can have any of the preferred or specific general meanings mentioned for the corresponding symbols in formula (I), and X represents a suitable anionic group deriving from a nucleophilic substitution reaction on the metal M;

with an organometallic compound having the following formula (V):

$$MT_t[(A_xD_yU_z)R']$$  (V)

wherein: the different symbols A, D, U, $R'$, "x", "y" and "z" can have any of the preferred or specific general meanings mentioned for the corresponding symbols in formula (II), and M' is a metal selected from metals of groups 1 or 2 of the periodic table of elements, T is any suitable organic or inorganic anion, or another group having the formula $(A_xD_yU_z)R'$, "t" has the value of 0 when M' is a metal of group 1, and the value of 1 when M' is a metal of group 2 of the periodic table.

until the desired compound having formula (I) is obtained.

Said process is suitably carried out, in accordance with the present invention, under relatively mild conditions, typical of organometallic reactions, preferably in the presence of a suitable inert solvent and at temperatures ranging from −60 to +100° C., more preferably from −20 to +40° C. The reaction is normally very rapid and is preferably completed in times ranging from 5 minutes to 2 hours, in relation to the other reaction parameters. Solvents suitable for the purpose are generally substances which do not react with the reagents used, and are liquid at the reaction temperature. Hydrocarbon solvents, such as cyclohexane, hexane, heptane, toluene, ethyl benzene are typical solvents of this type.

The precursor having formula (IV) and the organometallic compound having formula (V) are put in contact with each other with atomic ratios M'/M generally around the stoichiometric value of the reaction, i.e., for instance, 1/1, 2/1 or 3/1, depending on whether a complex comprising 1, 2 or 3 unsaturated oligomeric groups having formula (I), respectively, is to be obtained. This value can also be a decimal number between 1 and 3, if a product consisting of a mixture of complexes with a different number of oligomeric substituents, is required at the end. For example, if an equimolecular mixture of two complexes of bis(indenyl) zirconium, with one or two oligomeric substituents, respectively, is desired, the precursor bis(indenyl)ZrCl$_2$, for example, is reacted with the oligomeric salt, for instance Li(isoprene)$_6$Bu$^t$, with a salt/complex molar ratio of about 1.5, to obtain a mixture of complexes which can be schematically represented by the empirical formula bis(indenyl) Zr[(isoprene)$_6$]$_{1.5}$Cl$_{1.5}$.

In the case of the ratios 2/1 and 3/1, the structure of the precursor is more suitably selected so that 2 or 3 outgoing groups are respectively available on the metal M. A slight excess, up to 15% in moles, of organometallic compound (V), can favour the completion of the desired reaction.

The contact conditions of said two reagents are not particularly critical and can be chosen by experts in the field on the basis of the technical notes used in organometallic chemistry for effecting substitution reactions on complexes. Preferably, a solution of the compound having formula (V) is slowly added, under vigorous stirring, to a solution or suspension of the precursor having formula (IV). In general, it is always preferable to operate in such a way as to avoid the formation of local excesses of one of the two reagents.

In accordance with the above, said precursor having formula (IV) consists of a metallocene compound in which at least one X group is an outgoing group in the presence of an organometallic compound with strong anionic characteristics and a high nucleophilic nature, such as the compound having formula (V), which belongs to the group of metalloalkyls. X is generally a group capable of forming an anion with a low nucleophilic property. It can typically be a halide, such as chloride or bromide, an alkylsilyl $C_3$–$C_{20}$ group, an alkoxide or thioalkoxide $C_1$–$C_{20}$ group, a carboxylate or carbamate $C_2$–$C_{20}$ group, a dialkylamide $C_2$–$C_{20}$ group and a alkylsilylamide $C_4$–$C_{20}$ group. Typical examples are chloride or bromide, trimethyl silyl, triethyl silyl or tributyl silyl, methoxyl, ethoxyl, iso- or sec-butoxyl, ethyl sulfide, acetate, trifluoro-acetate, propionate, butyrate, pivalate, stearate, benzoate, diethyl amide, dibutyl amide, bis(trimethyl silyl) amide or ethyl trimethyl silylamide. Among the above products, the chloride group is preferred.

The other groups and substituents of the precursor having formula (IV), are correspondently selected by technical experts in the field on the basis of the structure of the metallocene complex having formula (I) which is to be obtained. If a metallocene complex, with two or three unsaturated oligomeric groups having formula (II), the same as each other, is to be obtained, the precursor having formula (IV) can be conveniently selected from the complexes in which the groups $R_6$ and R" also consist of one of the above outgoing groups, as defined for group X. In this case, $R_6$ and R" are preferably both chloride.

According to another version of the present process, it is also possible to prepare complexes having formula (I) with 2 or 3, preferably 2, unsaturated oligomeric groups having a different structure. For this purpose, the process is carried out in two or even three different steps, by reacting, in any step, a different organometallic compound having formula (V).

In some cases, when M is titanium, it has been observed that the organometallic compound (V) can have a reducing effect (through β-elimination) on the precursor having formula (IV), especially if used in excess with respect to the stoichiometric value, allowing a Ti(III) complex to be obtained, also starting from a precursor containing Ti(IV) and operating at relatively high temperatures, normally higher than 10° C. The complex of Ti(III) itself has been obtained starting from the corresponding precursor containing Ti(III). At temperatures lower than 10° C., on the contrary, and, more generally, with more stabilized titanium metallocene precursors, such as, for example, those containing two indenyl or pentamethyl cyclopentadienyl groups, it is possible to obtain complexes of titanium (IV) having formula (I) with two oligomeric groups. For an illustration of the different behaviour of titanium as a function of the reaction temperature, reference should be made to the following examples 8 and 9.

The metallocene precursor having formula (IV) can normally be prepared by means of one of the suitable methods, known in the art, for the synthesis of metallocene complexes of metals of group 4. These methods and their numerous variations are widely described in literature easily available to technical experts in the field, for instance in the above-mentioned "Comprehensive Organometallic Chemistry". Many Ti and Zr metallocene precursors, in which X and R" in formula (IV) represent chloride or methyl, are commercially available products.

The organometallic compound having formula (V) consists of an unsaturated hydrocarbyl metal wherein said anionic group $[(A_xD_yU_z)R^I]$ corresponds to said oligomeric group having formula (II). The metal M' can be an alkaline metal, such as lithium, sodium, potassium, or earth-alkaline such as magnesium or calcium. Lithium or sodium are preferred. If M' belongs to group 2, it is preferably magnesium and the complex having formula (V) comprises a second counter-anion T which preferably consists of an inorganic anion, especially a hydride or a halide, for example chloride or bromide, or it can be a second oligomeric hydrocarbyl group $[(A_xD_yU_z)R^I]$.

The organometallic compound having formula (V) is generally used, in practice, in the form of a solution in a hydrocarbon solvent, as obtained from the synthesis process, without isolating it as a pure compound. It is preferably prepared by means of one of the known living anionic polymerization techniques. Some of the very numerous publications on this matter are listed below, for illustrative purposes:

H. I. Hsieh, R. P. Quirk, Anionic Polymerization, Dekker Ed. (1996)
M. Morton, Anionic Polymerization: Principles and Practice, Academic Press, 1983
J. Mulvaney et alii, Advances in Polymer Science, 3 106 (1961)
W. Gebert at alli, Die Makromolekulare Chemie, 144, 97 (1971)
M. Morton et alii, J. Polym. Sci.: Part C, 1, 311 (1963)
M. Morton et alii, J. Polym. Sci.: Part A, 1, 1735 (1963)
F. M. Brower et alii, J. Polym. Sci.: Part A, 1, 1749 (1963)
A. Guyot et alii, J. Macromol. Sci.-Chem. A4(1) 107 (1970)

According to a preferred technique, the desired amount of polymerizable monomer is progressively added, under stirring, to a solution of a suitable initiator. The reaction proceeds with the typical so-called living anionic polymerization mechanism, as the anionic chain-end of the polymeric chain remains active during the reaction time and allows further amounts of monomer to be incorporated, even different from the initial monomer, if this is added to the reaction mixture. Oligomers made up of different monomeric blocks, or with a statistical distribution or consisting of blocks separated by sections of chains with a statistical distribution (tapered), can thus be formed. At the end, contrary to what is normally in use in the preparation of oligomers and polymers with this technique, the living polymer chain, forming said organometallic compound having formula (V), is not blocked, but is reacted as such with the metallocene precursor having formula (IV).

Said preparation is normally carried out according to the known technique, at temperatures between −80 and +80° C., preferably −30 and +20° C., in hydrocarbon solvents, possibly containing small amounts of aprotic polar compounds, such as tetrahydrofuran, to obtain particular distributions of the monomeric units in the chain.

Compounds having the formula $M'T_tR^I$ are suitable anionic polymerization initiators, wherein the meaning of M', T, "t" and $R^I$ is specified above. Examples of groups of these compounds are lithium alkyls, lithium aryls, sodium alkyls, magnesium alkylhalides (Grignard compounds). In some cases, still included in the present invention, the $R^I$ group can be a dianionic group bonded to two atoms of the metal M'. The use of these dianionic groups as initiators allows divalent oligomeric groups to be obtained, which, as already mentioned, are bonded to the metal M in the complex having formula (I), forming a cyclic structure including the same metal or, if reacted in the presence of a higher concentration of the metallocene precursor, can form binu-clear complexes. According to a known technique, the initiator can also be obtained by the reaction of a suitable unsaturated monomer, for example styrene or isoprene, with an alkaline metal, such as sodium or potassium. Also in this case dianionic initiators are formed.

Organic compounds of lithium, such as, for example, n-propyl lithium, isopropyl lithium, n-butyl lithium, sec-butyl lithium, tert-butyl lithium, n-pentyl lithium, benzyl lithium, 0,1,4-dilithium-n-butane, 1,5-dilithium pentane, 1,2-dilithium biphenyl ethane, are preferably used as initiators.

According to another technique, said organometallic compound having formula (V) can also be prepared by the metalation of an unsaturated oligomer conveniently prepared by means of any of the suitable polymerization or co-polymerization techniques of conjugated dienes, vinylaromatic compounds and possibly other co-polymerizable monomers mentioned above. Said techniques can be of the radicalic type, of the catalytic type, for example by means of the well-known Ziegler-Natta catalysts, including metallocene catalysts, or of the anionic type. The oligomers (sometimes, also with a relatively long chain) thus obtained are reacted with a suitable metalating agent, such as, for example, an alkaline metal or an alkyl compound of a metal of group 1 or 2 of the periodic table, to obtain the desired organometallic compound having formula (V).

The complexes having formula (I), in accordance with the present invention, are surprisingly stable over a long period of time, also at room temperatures or higher. This solves evident problems relating to preservation for long periods of time, which, on the other hand, create a serious drawback in the use of the other metallocene complexes, particularly metallocene alkyl complexes, known in the art.

The above complexes having formula (I) have also proved to be particularly advantageous in the formation of compositions with an excellent catalytic activity in the polymerization of olefins. In particular, they allow catalytic compositions to be prepared by means of reaction with the ionizing activators known in the art, without the addition of aluminum-alkyls, as organometallic co-activators, thus drastically reducing the amount of metal residues present in the olefin polymer obtained at the end of the process.

Other uses of the complexes of formula (I) have been found in the hydrogenation reaction of olefinically unsaturated compounds.

A further advantage of said complexes having formula (I) consists in the possibility of regulating the chain length of the oligomeric groups having formula (II) to the desired value, according to the above-mentioned procedure of the anionic polymerization technique. It is therefore possible to obtain complexes having formula (I) with optimal solubility in certain solvents, such as hydrocarbons, especially aliphatic hydrocarbons, due to the presence of an oligomeric group with a relatively long chain having lipophilic characteristics.

The present invention is further described by the following examples, which however are provided for solely illustrative purposes and in no way limit the overall scope of the invention.

EXAMPLES

The analytical techniques and characterization methods listed and briefly illustrated below are used in the following examples.

The characterization by means of $^1$H-NMR spectroscopy is carried out on a Bruker® MSL-300 nuclear magnetic resonance spectrophotometer.

FIGS. 1, 2, 3 and 4 enclosed herewith show the $^1$H-NMR spectra of some of the complexes obtained in accordance with the subsequent examples, for further characterization. Each figure also shows the most significant signals of the spectrum.

The characterization of the products and organic intermediates by means of gas-chromatography/mass spectrography (GC-Mass) was effected using a Finnigan® TSQ 700 instrument.

The measurement of the molecular weights of the olefin polymers and diene oligomers was effected by means of Gel-Permeation Chromatography (GPC). The analyses of the samples were carried out in 1,2,4-trichloro-benzene (stabilized with Santonox®) at 135° C. with a WATERS® 150-CV chromatograph, using a Waters differential refractometer as detector. The chromatographic separation was obtained using a set of $\mu$-Styragel HT (Waters) columns, three of which with a pore-size of $10^3$, $10^4$, $10^5$ Å, respectively, and two with a pore-size of $10^6$ Å, with an eluant flow-rate of 1 ml/min. The data were acquired and processed by means of Maxima 820 software version 3.30 (Millipore®); the calculation of the number average molecular weight (Mn) and weight average molecular weight (Mw) was effected by means of universal calibration, using calibration standards of polystyrene with molecular weights within the range of 6,500,000–2,000.

The characterization of the oligomeric products having formula (II) in the solutions prepared for the living anionic oligomerization, was effected by taking an aliquot which is quenched with MeOH and HCl at 37% and extracted with CH$_2$Cl$_2$. The organic extract is washed with water until a neutral pH is reached, anhydrified on Na$_2$SO$_4$, filtered and the solvent evaporated; an oil is obtained which is analyzed by means of the above-mentioned GPC and $^1$H-NMR techniques. The NMR characterization is based on known techniques, for example according to what is described in the publications: J. A. Frankland et alii, Spectrochimica Acta; vol 47A Nr 11, pages 1511–24 (1991); H. Sato et alii, J. Polym. Sci.: Polymer Chemistry, vol 17, pages 3551–58 (1979); T. Suzuki et alii, JACS, vol 11(4), 639 (1978); H. Tanaka et alii, Polymer, vol 17, 113 (1976).

The EPR characterization was carried out with a Brucker WSP300E spectrometer. The solutions of the samples in toluene were analyzed as such, by simple transfer into the sample-holder tube, at room temperature.

During the preparations listed in the examples, the following reagents were used:
methyllithium (LiMe) 1.6 M in diethyl ether (ALDRICH);
n-butyllithium (LiBu) 2.5 M in hexane (ALDRICH);
t-butyllithium (LiBu$^t$) 1.5 M in pentane (ALDRICH);
triisobutylaluminum (TIBAL) (CROMPTON);
(pentamethyl-$\eta^2$-cyclopentadienyl)titanium(IV) trichloride [Cp*TiCl$_3$] (CROMPTON);
1,2-ethylen-bis(indenyl)zirconium dichloride (et(ind)$_2$ZrCl$_2$] (CROMPTON);
bis cyclopentadienyl titanium dichloride [Cp$_2$TiCl$_2$] (CROMPTON);
methylaluminoxane (MAO) (10% (weight Al)/volume in toluene) (CROMPTON);
isoprene (polymerization grade) (ALDRICH), distilled on NaH under argon;
styrene (polymerization grade) (ALDRICH), distilled at low pressure on CaH$_2$.

The reagents and/or solvents used which do not appear in the above list, are those commonly adopted in laboratory practice and on an industrial scale, and can therefore be easily found on the specialized market. In performing the operations described in the examples, the procedures and precautions of standard practice were observed, particularly for reactions effected with organometallic compounds in an inert atmosphere and with anhydrous solvents.

Preparative Example

In a series of tests for establishing the reproducibility of the preparation of oligomers by means of living polymerization, an excellent concordance between the theoretical value of the polymerization grade (moles of monomer/moles of initiator charged) and the experimental value measured by means of the above-mentioned characterization techniques, was observed. In a typical preparation of an oligomer having an average polymerization degree of 6.3, 17 ml of a 1.5 M solution of butyl lithium (4.76 mmoles) in pentane are charged, under stirring, into a test-tube containing 10 ml of anhydrous hexane. 1.95 g (28.56 mmoles) of freshly distilled isoprene on NaH (Isoprene/Li= 6) are added dropwise to the solution, cooled with a water/ice bath. When the addition of isoprene is terminated, the mixture is heated to room temperature, under stirring. The oligomerization reaction is rapidly completed during the heating. An aliquot of the solution is removed and analyzed as specified above. Both 1–4 and 1–2 monomeric units were found, deriving from polymerization with addition, according to the typical distribution of anionic polymerization. An excellent concordance (average deviation lower than 10%) between the theoretical value of the polymerization grade (moles of monomer/moles of t-butyllithium) and the measured value, were found.

Example 1

Operating in accordance with the above preparative example, 3.17 ml of a 1.5 M solution of t-butyllithium (4.76 mmoles) in pentane, are charged, under stirring, into a test-tube containing 10 ml of anhydrous hexane. 1.95 g (28.56 mmoles) of isoprene (isoprene/Li ratio=6) are slowly added to the solution, cooled with a water/ice bath. Once the addition of isoprene is terminated, the mixture is heated to room temperature, under stirring. A solution of lithium polyisoprenyl with an average polymerization degree of 6 is obtained. A suspension of 0.9 g (2.14 mmoles) of Et(Ind)$_2$ZrCl$_2$ in 50 ml of toluene is slowly added to the solution. The mixture is left under stirring for 5 hours. The solution is filtered on a G4 porous septum. The solvent is then removed by evaporation under vacuum, obtaining 2.3 g of a waxy, orange-coloured solid, which, upon characterization, proved to essentially consist of an Et(Ind)$_2$Zr(polyisoprenyl)$_2$ complex with an average polymerization degree of isoprene equal to 6 (yield 84%), called "Zr(I6)$_2$ complex".

Elemental analysis for C$_2$H$_4$(C$_9$H$_6$)$_2$Zr[(C$_5$H$_8$)$_6$C$_4$H$_9$]$_2$ (molecular weight 1279.2)

Theoretical: Zr=7.13%

Found: Zr=7.10%

The $^1$H-NMR spectrum of the complex thus obtained, measured in a solution of toluene subjected to deuteration, is shown in FIG. 1.

Example 2

The procedure of the previous example 1 is reproduced, operating with the same reagents and in the same proportions, but using 1.8 g (4.28 mmoles) of Et(Ind)$_2$ZrCl$_2$ suspended in about 70 ml of toluene, instead of 0.9 g previously used, so as to obtain, at the end, a complex essentially containing only one unsaturated oligomeric group. The solution is left under stirring for 5 hours and is then filtered on a G4 porous septum. The solvent is then removed by evaporation under vacuum, obtaining about 3 g of a waxy, orange-coloured solid, which, upon characterization, proved to essentially consist of an Et(Ind)$_2$Zr(polyisoprenyl)Cl complex with an average polymerization degree of isoprene equal to 6 (yield 84%), called "ZrI6 complex".

Elemental analysis for C$_2$H$_4$(C$_9$H$_6$)$_2$ZrCl(C$_5$H$_8$)$_6$C$_4$H$_9$ (molecular weight 848.8)

Theoretical: Zr=10.75%, Cl=4.18%

Found: Zr=10.3%, Cl=4.22%

The $^1$H-NMR spectrum of the complex thus obtained, measured in a solution of toluene subjected to deuteration, is shown in FIG. 2.

Example 3

Operating with the same procedure in accordance with the above Preparative Example, 1.76 ml (3 mmoles) of a 1.7 M solution in pentane of t-butyllithium are charged, under stirring, into a test-tube containing 2.1 ml of anhydrous cyclohexane and 0.6 ml (6 mmoles) of isoprene (isoprene/Li=2). The solution is left under stirring for about 2.5 hours and a suspension of 0.567 g (1.35 mmoles) of Et(Ind)$_2$ZrCl$_2$ in about 25 ml of toluene is slowly added to the solution. The mixture, which immediately becomes orange-coloured, is left under stirring for 5 hours. It is filtered on a porous septum (G4) in an inert atmosphere; the filtrate is evaporated under vacuum, obtaining about 0.83 g of a waxy, orange-coloured solid, which, upon characterization, proved to essentially consist of an Et(Ind)$_2$Zr(polyisoprenyl)$_2$ complex with an average polymerization degree of isoprene equal to 2 (yield 84%), called "Zr(I2)$_2$ complex".

Elemental analysis for C$_2$H$_4$(C$_9$H$_6$)$_2$Zr[(C$_5$H$_8$)$_2$C$_4$H$_9$]$_2$ (molecular weight=734)

Theoretical: Zr=12.4%

Found: Zr=12.4%

The $^1$H-NMR spectrum of the complex thus obtained, measured in a solution of toluene subjected to deuteration, is shown in FIG. 3.

Example 4

Operating with the same procedure in accordance with Preparative Example above, 5.1 ml (8 mmoles) of a 1.57 M solution in pentane of t-butyllithium are charged, under stirring, into a test-tube containing 13.6 ml of anhydrous cyclohexane and 4 ml (40 mmoles) of isoprene (isoprene/Li=5). The solution is left under stirring for about 3 hours. A suspension of 1.67 g (4 mmoles) of Et(Ind)$_2$ZrCl$_2$ (Li—R/Zr=2) in toluene (about 50 ml) is slowly added to the solution. The mixture, which immediately becomes orange-coloured, is left under stirring for 5 hours. It is filtered on a porous septum (G4) in an inert atmosphere; the filtrate is evaporated under vacuum, obtaining about 3.9 g of a waxy, orange-coloured solid, which, upon characterization, proved to essentially consist of an Et(Ind)$_2$Zr(polyisoprenyl)$_2$ complex with an average polymerization degree of isoprene equal to 5 (yield 85%), called "Zr(I5)$_2$ complex".

Elemental analysis for C$_2$H$_4$(C$_9$H$_6$)$_2$Zr[(C$_5$H$_8$)$_5$C$_4$H$_9$]$_2$ (molecular weight=1143)

Theoretical: Zr=7.98%

Found: Zr=8.0%

Example 5

Operating with the same procedure in accordance with the above Preparative Example, 2.55 ml (4 mmoles) of a 1.57 M solution in pentane of t-butyllithium are charged, under stirring, into a test-tube containing 13.6 ml of anhydrous cyclohexane and 4 ml (40 mmoles) of isoprene (isoprene/Li=10). The solution is left under stirring for about 3 hours. A suspension of 0.84 g (2 mmoles) of Et(Ind)$_2$ZrCl$_2$ (Li—R/Zr=2) in toluene (about 30 ml) is slowly added to the solution. The mixture, which immediately becomes orange-coloured, is left under stirring for 5 hours. It is filtered on a porous septum (G4) in an inert atmosphere; the filtrate is evaporated under vacuum, obtaining about 3.13 g of a waxy, orange-coloured solid, which, upon characterization, proved to essentially consist of an Et(Ind)$_2$Zr(polyisoprenyl)$_2$ complex with an average polymerization degree of isoprene equal to 10 (yield 86%), called "Zr(I10)$_2$ complex".

Elemental analysis for C$_2$H$_4$ (C$_9$H$_6$)$_2$Zr[(C$_5$H$_8$)$_{10}$C$_4$H$_9$]$_2$ (molecular weight=1824)

Theoretical: Zr=5.00%

Found: Zr=4.93%

Example 6

Operating with the same procedure in accordance with the above Preparative Example, 5.1 ml (8 mmoles) of a 1.57 M solution in pentane of t-butyllithium are charged, under stirring, into a test-tube containing 13.6 ml of anhydrous cyclohexane and 4 ml (40 mmoles) of isoprene freshly distilled on NaH (isoprene/Li=5). The solution is left under stirring for about 3 hours. A suspension of 2.18 g (4 mmoles) of o-benzylidene bis-($\eta^5$-1-indenyl) zirconium dichloride (formula C$_6$H$_4$CH$_2$(Ind)$_2$ZrCl$_2$, obtained in accordance with the synthesis procedure described in example 1 of Italian patent nr. 1298616 (granted to the Applicant)] in about 50 ml of toluene is slowly added to the solution. The mixture is left under stirring for 5 hours and is then filtered on a porous septum (G4) in an inert atmosphere; the filtrate is evaporated under vacuum, obtaining about 4.27 g of a waxy, orange-coloured solid is obtained, which, upon characterization, proved to essentially consist of an o-benzylidene bis-($\eta^5$-1-indenyl)Zr(polyisoprenyl)$_2$ complex with an average polymerization degree of isoprene equal to 5 (yield 84%), called "ZrBz(I5)$_2$ complex".

Elemental analysis for $C_6H_4CH_2(C_9H_6)_2Zr[(C_5H_8)_5C_4H_9]_2$ (molecular wieght=1205)

Theoretical: Zr=7.57%

Found: Zr=7.38%

Example 7

1.65 ml (2.8 mmoles) of a 1.7 M solution in pentane of t-butyllithium are charged, under stirring, into a test tube containing 2 ml of anhydrous cyclohexane. 0.38 g (5.6 mmoles) of isoprene are added dropwise to the solution, under stirring. A solution, obtained by dissolving 0.6 g (2.8 mmoles) of bis(cyclopentadienyl)titanium(III) chloride [formula $Cp_2TiCl$ ($Cp=C_5H_5$); prepared from $Cp_2TiCl_2$ according to the procedure described in the publication "Inorganic Synthesis", vol. 21, page 84] in 40 ml of toluene, is slowly added to the solution. The mixture is left under stirring for 2 hours and the colour changes from red to purple. The solution is filtered on a G4 porous septum and the solvent is removed by evaporation under vacuum; 1 g of a purple-coloured solid is obtained, which, upon characterization, proved to essentially consist of a bis-($\eta^5$-cyclopentadienyl)Ti(polyisoprenyl) complex with an average polymerization degree of isoprene equal to 2, called "TiI2 complex".

Elemental analysis for $Cp_2Ti[(C_5H_8)_2C_4H_9]$ (molecular weight=371)

Theoretical: Ti=12.9%

Found: Ti=12.8%

Example 8

3.2 ml of a 1.5 M solution in pentane of t-butyllithium (4.8 mmoles) are charged, under stirring, into a test-tube containing 3.4 ml of anhydrous cyclohexane. 0.655 g (9.6 mmoles) of isoprene are added dropwise to the solution, under stirring. A solution of 0.55 g (2.2 mmoles) of $Cp_2TiCl_2$ in 25 ml of toluene, is slowly added to the solution. The mixture is left under stirring overnight, at room temperature. The colour changes from red to purple. The solution is filtered on a G4 porous septum and the solvent is removed by evaporation under vacuum, obtaining 0.8 g of a purple-coloured solid, which, upon characterization, proved to essentially consist of a bis-($\eta^5$-cyclopentadienyl)Ti (polyisoprenyl) complex with an average polymerization degree of isoprene equal to 2, essentially analogous to the TiI2 complex obtained in accordance with the previous example 7. From EPR measurements, it was found that all the titanium is in oxidation state (III). We believe that during the preparation reaction, the titanium is reduced from oxidation state (IV) to state (III) through β-elimination, analogously to what is generally known with respect to titanium cyclopentadienyl dialkyl complexes.

Elemental analysis for $Cp_2Ti[(C_5H_8)_2C_4H_9]$ (molecular weight=371)

Theoretical: Ti=12.89%

Found: Ti=12.79%

Example 9

3.2 ml (4.8 mmoles) of a 1.5 M solution in pentane of t-butyllithium are charged, under stirring, into a test-tube containing 3.4 ml of anhydrous cyclohexane. 0.655 g (9.6 mmoles) of isoprene are added dropwise to the solution, under stirring. A solution of 0.55 g (2.2 mmoles) of $Cp_2TiCl_2$ in 25 ml of toluene, is slowly added to the solution, cooled to about 0° C. with a water/ice bath and shielded from the light with an aluminum foil. The mixture is left under stirring overnight. The colour changes from red to dark brown. The solution is filtered on a G4 porous septum and the solvent is removed by evaporation under vacuum; 0.9 g of a brown-coloured solid are obtained, which, upon characterization by means of EPR and $^1$H NMR, proved to essentially consist of a bis-($\eta^5$-cyclopentadienyl)Ti(IV) (polyisoprenyl) 2 complex with about 5% of the corresponding complex of Ti(III), in which the polyisoprenyl group has an average polymerization degree of isoprene equal to 2.

By effecting the reaction at a low temperature and with photo-protection, the η-elimination reaction was inhibited, thus prevalently obtaining the desired Ti(IV) complex.

Elemental analysis: Ti=8.7%

EPR analysis: Ti(III) 5%

The $^1$H-NMR spectrum of the complex thus obtained, measured in a solution of toluene subjected to deuteration, is shown in FIG. 4.

Example 10

3.35 ml (5.7 mmoles) of a 1.5 M solution in pentane of t-butyllithium are charged, under stirring, into a test-tube containing 4 ml of anhydrous cyclohexane. 0.78 g (11.4 mmoles) of isoprene are added dropwise to the solution, under stirring. A solution of 0.55 g (1.9 mmoles) of (pentamethyl-$\eta^5$-cyclopentadienyl) titanium(IV) trichloride [formula $Cp^*TiCl_3$, ($Cp^*=C_5(CH_3)_5$)] in 15 ml of toluene, is slowly added to the solution. The mixture is left under stirring overnight. The solution is filtered on a G4 porous septum and the solvent is removed by evaporation under vacuum; 1.3 g of a brown-coloured solid are obtained, which, upon characterization, proved to essentially consist of a tris-$(Cp^*)$Ti(polyisoprenyl)$_3$ complex with an average polymerization degree of isoprene equal to 2, called "Ti(I2)$_3$ complex".

Elemental analysis for $Cp^*Ti[(C_5H_8)_2C_4H_9]_3$ (molecular weight=763)

Theoretical: Ti=6.27%

Found: Ti=6%

Example 11

1.65 ml (2.8 mmoles) of a 1.7 M solution in pentane of t-butyllithium are charged, under stirring, into a test-tube containing 2 ml of anhydrous cyclohexane. 0.95 g (14 mmoles) of isoprene are added dropwise to the solution, under stirring. A suspension obtained by dispersing 0.6 g (2.8 mmoles) of $Cp_2TiCl$ (prepared as described in the previous example 7) in 40 ml of toluene, is slowly added to the solution. The mixture is left under stirring for two hours. The solution is filtered on a G4 porous septum and the solvent is removed by evaporation under vacuum; 1.55 g of a waxy solid are obtained, which, upon characterization, proved to essentially consist of a $(Cp)_2Ti(polyisoprenyl)$ complex with an average polymerization degree of isoprene equal to 5, called "Ti(I5) complex".

Elemental analysis for $Cp_2Ti[(C_5H_8)_5C_4H_9]$ (molecular weight=575.78)

Theoretical: Ti=8.32%

Found: Ti=8.3%

Example 12

2 ml of butadiene (about 24 mmoles), dried by passage through a column filled with molecular sieves, are condensed in a glass tailed tube kept at −20° C. 8.5 ml of cyclohexane are then added to the butadiene. 3 ml (4.8 mmoles) of a 1.57 M solution of t-butyllithium in pentane are charged, under stirring, into a reactor at room temperature. The mixture is left under stirring for about two hours. A suspension (obtained as shown above) of 1.025 g (4.8 mmoles) of $(Cp)_2TiCl$ in 25 ml of toluene, is slowly added to the solution. The mixture is left under stirring for 5 hours and is then filtered on a porous septum (G4), in an inert atmosphere; the filtrate is evaporated under vacuum and about 2 g of a waxy solid are obtained, which, upon characterization, proved to essentially consist of a $(Cp)_2Ti$ (polybutadienyl) complex, with an average polymerization degree of butadiene equal to 5, called "Ti(B5) complex".

Elemental analysis for $(C_5H_5)_2Ti[(C_4H_6)_5C_4H_9]$ (molecular weight=505.64)

Theoretical: Ti=9.47%

Found: Ti=9.53%

Example 13

Polymerization of Ethylene

All the preparative operations for carrying out the polymerization tests are effected in vessels subjected to vacuum, interrupted by three flushings with nitrogen for at least two hours, and in a nitrogen atmosphere; the reaction solvent (toluene or heptane) was distilled on sodium metal and preserved on molecular sieves; all other solvents were used as such.

500 ml of anhydrous toluene and 0.75 mmoles of TIBAL, as impurity scavenger, are charged, under a nitrogen flow, into a steel autoclave having a volume of 1 l, washed with a solution of aluminum triisobutyl in toluene and dried at a high temperature, under vacuum. The whole mixture is thermo-regulated at 50° C. and at this point, 10 ml of a toluene solution containing $2.5 \cdot 10^{-3}$ mmoles of "$Zr(I2)_2$ complex", prepared according to the previous example 3, and $2.5 \cdot 10^{-3}$ mmoles (2.3 mg) of $B(C_6F_5)_4CPh_3$ are charged, under a nitrogen flow, into the autoclave. After introducing the catalytic system, the autoclave is pressurized at 80 KPa (rel.) with ethylene, maintaining the pressure constant for 30 minutes. At the end, the autoclave is de-pressurized and the polymerization is blocked with methanol. The polymer is recovered by precipitation in two liters of methanol with hydrochloric acid, filtration and drying under vacuum at 40° C. for about 8 hours. 50 g of polyethylene are obtained, with a number average molecular weight (Mn) of 95,000 and a weight average molecular weight (Mw) of 200,000, with an average dispersion MWD=Mw/Mn of 2.1.

Example 14

Polymerization of Ethylene 98.5 ml of toluene containing 1 mmole/l of TIBAL as impurity scavenger, are charged into a 250 ml glass reactor, equipped with a magnetic stirrer and thermostat-regulated at 50° C. 10 ml of a toluene solution are added, under a nitrogen flow, containing $1.5 \cdot 10^{-3}$ mmoles of "$Zr(I2)_2$ complex" and $1.5 \cdot 10^{-3}$ mmoles (0.71 mg) of 1,2,3,4,5,6,7,8-octafluoro-9-(pentafluorophenyl)fluorene (PFF), prepared as described in example 8 of the mentioned European patent application nr.1,013,675.

The reactor is pressurized at 50 KPa (rel.) with ethylene and the mixture is maintained under stirring for 60 minutes at 50° C., continuously feeding ethylene to maintain the pressure constant at the initial value. At the end, the reactor is depressurized and 5 ml of methanol are introduced to complete the polymerization and deactivate the catalyst. The polymer is recovered by precipitation in 400 ml of methanol acidified with hydrochloric acid, filtration and drying under vacuum at 40° C. for about 8 hours. 15 g of polyethylene are obtained, with Mw=186,000, Mn=77,200 and MWD=2.4.

Example 15

Ethylene/1-Hexene Copolymerization

A solution of the polymerization catalyst according to the present invention is prepared separately, by dissolving 61 mg (0.048 mmoles) of the "TiI2 complex", prepared according to the previous example 7, in 53 ml of anhydrous toluene, and adding 0.048 mmoles (44 mg) of $B(C_6F_5)_4CPf_3$ to this mixture, at room temperature, so that the atomic ratio B/Zr is equal to about 1. The catalyst solution thus prepared is left to mature, leaving it under stirring for 10 minutes at room temperature, before introducing it into the polymerization mixture.

900 ml of toluene (previously distilled on sodium metal), 60 ml of 1-hexene (previously distilled on calcium hydride $CaH_2$) and 1.5 mmoles of TIBAL as impurity scavenger, are charged into a BUCHI 2 liter glass autoclave, equipped with a helix stirrer and thermostatic jacket, maintained under vacuum for at least two hours, interrupted by three flushings with nitrogen. The autoclave is pressurized with ethylene at 0.2 MPa and is heated to a temperature of 40° C.

The autoclave is depressurized and 1.1 ml of the catalyst solution, prepared as above, are charged under an ethylene flow. The autoclave is again pressurized to 2 atm with ethylene and the polymerization is carried out for 30 minutes, by thermostat-regulating the temperature at 40° C. and continuously feeding ethylene to keep the pressure constant during the test. At the end, the reaction is interrupted by adding 5 ml of methanol acidified with hydrochloric acid, the autoclave is depressurized and the polymer is recovered by precipitation with 3 liters of acidified methanol and subsequent washing with acetone. 10 g of an ethylene/1-hexene (LLDPE) copolymer are obtained after drying, having the following characteristics:

number average molecular weight (Mn) 123,000 and weight average molecular weight (Mw) 330,000 molecular weight distribution (MWD=Mw/Mn): 2.7 monomeric units deriving from 1-hexene (1-hexene inserted): 8% monomer reactivity product $(r_1 \cdot r_2)$: 0.64.

Example 16

Ethylene Polymerization with a Catalyst Prepared 6 Months Before and Preserved in a Refrigerator 500 ml of anhydrous toluene and 0.75 mmoles of TIBAL as impurity scavenger, are charged, under a nitrogen flow, into a 1 liter steel autoclave, washed with a solution of aluminum triisobutyl in toluene and dried at a high temperature and under vacuum. The liquid is thermostat-regulated at a temperature of 50° C. and 10 ml of a toluene solution, containing $2.5 \cdot 10^{-3}$ mmoles of aged "$Zr(I2)_2$ complex", prepared according to the previous example 3 and preserved in a refrigerator at +5° C. for six months, are charged under a nitrogen flow. $2.5 \cdot 10^{-3}$ mmoles (2.3 mg) of $B(C_6F_5)_4CPh_3$ are then added and the autoclave is pressurized at 80 KPa (rel.) with ethylene, the pressure being maintained constant for the following 30 minutes by the continuous feeding of ethylene. At the end, the autoclave is depressurized and the reaction is stopped with methanol. The polymer is recovered by precipitation, by pouring the polymerization mixture into 2 liters of methanol acidified with hydrochloric acid and maintaining under vigorous stirring. After filtration and drying under vacuum at 40° C. for about 8 hours, 48 g of polyethylene are obtained, having Mn=95,300, Mw=195,000 and MWD=2.05.

Other embodiments and variations of the present invention, different from those specifically described and illustrated above, are however possible and accessible to technical experts in the art.

What is claimed is:

1. A metallocene complex of a metal of group 4 of the periodic table having the following formula (I):

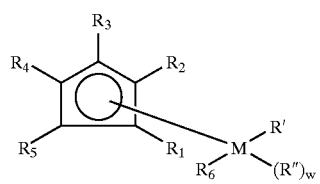

(I)

wherein:
M is a metal selected from the group, consisting of titanium, zirconium and hafnium, coordinatively bonded to a first $\eta^5$-cyclopentadienyl group;
R' represents an unsaturated hydrocarbyl group;
R" represents a group anionically bonded to the metal M, consisting of an organic or inorganic radical, different from cyclopentadienyl or substituted cyclopentadienyl;
the groups $R_1$, $R_2$, $R_3$, $R_4$ and $R_5$, each independently represents, an atom or radical bonded to said first $\eta^5$-cyclopentadienyl group, and is selected from the group consisting of hydrogen, organic groups and inorganic groups;
$R_6$ represents an organic or inorganic group, anionically bonded to the metal M;
"w" has the value of 0 or 1,
wherein said R' group consists of an unsaturated oligomeric group having the following formula (II):

(II)

wherein:
A represents any monomeric unit derived from a vinylaromatic group polymerizable by means of anionic polymerization, having from 6 to 20 carbon atoms;
D represents any monomeric unit derived from a conjugated diolefin polymerizable by means of anionic polymerization, having from 4 to 20 carbon atoms;
U represents any generic monomeric unit derived from an unsaturated compound co-polymerizable with any of the above conjugated diolefins D or vinylaromatic compounds A;
$R^I$ hydrogen or a hydrocarbyl group having from 1 to 20 carbon atoms;
each index "x" and "y" can be independently zero or an integer, provided the sum (x+y) is equal to or higher than 2;
"z" can be zero or an integer ranging from 1 to 20;
with the proviso that, when $R_6$ is a $\eta^5$-cyclopentadienyl or substituted $\eta^5$-cyclopentadienyl group and R' is $-(A_x)$ $R^I$, R" is different from $-(A_x) R^I$.

2. The metallocene complex according to claim 1, wherein the metal M is selected from the group consisting of titanium and zirconium.

3. The metallocene complex according to claim 1, wherein the metal M is titanium in oxidation state +3 and "w" in formula (I) is equal to 1.

4. The metallocene complex according to claim 1, wherein M is zirconium in oxidation state +4 and "w" in formula (I) is 1.

5. The metallocene complex according to claim 1, wherein said monomeric units of the D type in formula (II) derive from 1,3-diolefins having from 4 to 20 carbon atoms.

6. The metallocene complex according to claim 5, wherein said 1,3-diolefin is selected from the group consisting of 1,3-butadiene, isoprene, 1,3-pentadiene, 2-methyl-1,3-pentadiene and 1,3-hexadiene.

7. The metallocene complex according to claim 1, wherein said monomeric units of the A type in formula (II) derive from vinylaromatic hydrocarbyl compounds having from 8 to 15 carbon atoms.

8. The metallocene complex according to claim 7, wherein said vinylaromatic compound is selected from the around consisting of styrene, α-methylstyrene, p-methylstyrene, and vinylnaphthalene.

9. The metallocene complex according to claim 1, wherein said sum (x+y) of the indexes in formula (II) is between 2 and 15.

10. The metallocene complex according to claim 1, wherein the sum of the indexes (x+y+z) in formula (II) is between 2 and 15.

11. The metallocene complex according to claim 1, wherein "z" in formula (II) is equal to 0.

12. The metallocene complex according to claim 1, wherein "x" and "z" in formula (II) are both equal to 0 and said group R' consists of an oligomer of a conjugated diene D with an average polymerization degree from 2 to 15.

13. The metallocene complex according to claim 1, wherein said group $R^I$ in formula (II) represents an aliphatic, cycloaliphatic, aromatic or alkyl aromatic group having from 2 to 10 carbon atoms.

14. The metallocene complex according to claim 1, wherein said group R" or said group $R_6$ are independently selected from the group consisting of hydrogen, halogen, an alkyl $C_1$–$C_{20}$ group, an alkyl aryl $C_1$–$C_{20}$ group, an allyl $C_3$–$C_{20}$ group, an alkyl silyl $C_3$–$C_{20}$, group, a cycloalkyl $C_5$–$C_{20}$ group, an aryl $C_6$"$C_{20}$ group, an aryl alkyl $C_6$–$C_{20}$ group, an alkoxide $C_1$–$C_{20}$ group, a thioalkoxide $C_1$–$C_{-20}$ group, a carboxylate $C_2$–$C_{20}$ group, a carbamate $C_2$–$C_{20}$ group, a dialkyl amide $C_2$–$C_{20}$ group and an alkyl silylamide $C_4$–$C_{20}$ group.

15. The metallocene complex according to claim 1, wherein both said groups R' and R" in formula (I) are independently oligomeric groups having formula (II).

16. The metallocene complex according to claim 1, wherein said group $R_6$ is bridge-bonded to said first cyclopentadienyl group having formula (I) to form an overall cyclic structure including the metal M.

17. The metallocene complex according to claim 1, wherein said group $R_6$ represents a second cyclopentadienyl group $\eta^5$-coordinated to the metal M.

18. The metallocene complex according to claim 17, wherein said first and second cyclopentadienyl group are equal to each other.

19. The metallocene complex according to claim 1, wherein said group $R_6$ represents a further oligomeric group having formula (II).

20. The metallocene complex according to claim 1, also comprising one or more neutral coordinating compounds.

21. A process for the preparation of a metallocene complex according to claim 1, comprising the contact and reaction, of a metallocene precursor having the following formula (IV):

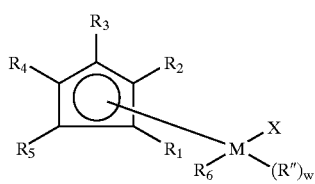

wherein: the symbols M, R", $R_1$, $R_2$, $R_3$, $R_4$, $R_5$, $R_6$, and "w" can have any of the meanings for the corresponding symbols in formula (I), according to claim 1, and X represents an outgoing anionic group in a nucleophilic substitution reaction on the metal M;

with an organometallic compound having the following formula (V):

$$MT_t[(A_xD_yU_z)R^I] \qquad (V):$$

wherein:
the symbols A, D, U, $R^I$, "x", "y" and "z" can have any of the meanings for the corresponding symbols in formula (II) of claim 1, m' is a metal selected from the group consisting of metals of groups 1 and 2 of the periodic table of elements, T is any organic or inorganic anion, or another group having the formula $(A_xD_yU_z)$ $R^I$, "t" has the value of 0 when M' is a metal of group 1, and the value of 1 when M' is a metal of group 2 of the periodic table, until the compound having formula (I) is obtained.

22. The process according to claim 21, carried out in the presence of an inert solvent, and at a temperature ranging from −60 to +100° C.

23. The process according to claim 22, carried out at a temperature ranging from −20 to +40° C., for a period of 5 minutes to two hours.

24. The process according to claim 22, wherein said solvent is selected from the group consisting of cyclohexane, hexane, heptane, toluene and ethyl benzene.

25. The process according to claim 21, wherein said organometallic compound having formula (V) is added to the precursor having formula (IV) in an inert solvent.

26. The process according to claim 21, wherein said organometallic compound having formula (V) is obtained by means of a living anionic polymerization reaction.

27. The process according to claim 26, wherein said organometallic compound having formula (V) is used as obtained in a preparation solution thereof.

28. The process according to claim 21, wherein said precursor having formula (IV) and said organometallic compound having formula (V) are put in contact with each other with atomic ratios M'/M close to the stoichiometric value and up to a molar excess of 15% of M' with respect to M.

29. The process according to claim 21, wherein in said precursor having formula (IV), said outgoing group X is selected from the group consisting of a chloride group, a bromide group, an alkyl silyl $C_3$–$C_{20}$ group, an alkoxide $C_1$–$C_{20}$ group, a thioalkoxide $C_1$–$C_{20}$ group, a carboxylate $C_2$–$C_{20}$ group, a carbamate $C_2$–$C_{20}$ group, a dialkyl amide $C_2$–$C_{20}$ group and a alkyl silylamide $C_4$–$C_{20}$ group.

30. The process according to claim 29, wherein said X group in formula (IV) is chloride or bromide.

31. The process according to claim 21, wherein the symbols X and R" in said precursor having formula (IV) both represent an outgoing anionic group.

32. The process according to claim 21, wherein the symbols X, R' and $R_6$ in said precursor having formula (IV) all independently represent an outgoing anionic group.

33. The process according to claim 21, wherein said metal M' in the compound having formula (V) is selected from the group consisting of lithium, sodium and magnesium.

34. Metallocene complex according to claim 1, wherein at least one of said groups R', R" and $R_6$ includes an olefinically unsaturated double bond.

35. The metallocene complex according to claim 13, wherein said group $R^I$ in formula (II) is selected from the group consisting of tert-butyl, n-butyl, isopropyl, n-hexyl, cyclohexyl, benzyl, phenyl and toluyl.

36. The metallocene complex according to claim 15, wherein groups R' and R" essentially have the same formula.

37. The process according to claim 22, wherein the inert solvent is a hydrocarbon.

38. The process according to claim 31, wherein X and R" are both chloride.

39. The process according to claim 32, wherein X, R" and $R_6$ are all chloride.

40. The process according to claim 33, wherein M' is lithium.

41. A catalytic composition comprising the metallocene complex according to claim 1, and a co-catalyst.

42. A process comprising (co)polymerization of an α-olefin in the presence of the metallocene complex according to claim 1.

43. A process comprising hydrogenation of an ethenically unsaturated compound in the presence of the metallocene complex according to claim 1.

* * * * *